(12) United States Patent
Larsen et al.

(10) Patent No.: US 8,877,485 B2
(45) Date of Patent: Nov. 4, 2014

(54) APPARATUS AND METHOD FOR PROCESSING BIOLOGICAL SAMPLES

(75) Inventors: Søren Damgaard Larsen, Glostrup (DK); Peter Axel Valbjørn, Ballerup (DK)

(73) Assignee: Dako Denmark A/S (DK)

( * ) Notice: Subject to any disclaimer, the term of this patent is extended or adjusted under 35 U.S.C. 154(b) by 1001 days.

(21) Appl. No.: 12/962,825

(22) Filed: Dec. 8, 2010

(65) Prior Publication Data

US 2011/0136135 A1 Jun. 9, 2011

Related U.S. Application Data

(60) Provisional application No. 61/267,906, filed on Dec. 9, 2009.

(51) Int. Cl.
  *C12M 1/34* (2006.01)
  *G01N 1/28* (2006.01)
  *G01N 1/31* (2006.01)
  *G01N 35/00* (2006.01)

(52) U.S. Cl.
  CPC .............. *G01N 1/2813* (2013.01); *G01N 1/312* (2013.01); *G01N 35/00029* (2013.01)
  USPC ....................................................... 435/288.3

(58) Field of Classification Search
  None
  See application file for complete search history.

(56) References Cited

U.S. PATENT DOCUMENTS 7,476,543 B2 * 1/2009 Becker et al. .................... 436/43
8,058,010 B2 * 11/2011 Erickson et al. ............... 435/7.1

* cited by examiner

*Primary Examiner* — Ann Lam
(74) *Attorney, Agent, or Firm* — Finnegan, Henderson, Farabow, Garrett & Dunner LLP.

(57) ABSTRACT

A method and an automated apparatus for processing at least one biological sample arranged on a slide. At least one capillary staining module has a slide rack holder configured to detachably hold a slide rack configured to hold slides, and a capillary lid rack holder configured to detachably hold a capillary lid rack configured to hold capillary lids, wherein the slide rack can be removed independently of removing the capillary lid rack. A first fluid container has a first fluid. The apparatus being configured to automatically rotate the one or more slides, and to move the lids towards the slides to automatically form a capillary gap between each slide and each capillary lid, said capillary gap functioning as a capillary chamber; and to supply an amount of the first fluid to the slide.

43 Claims, 18 Drawing Sheets

APPARATUS AND METHOD FOR PROCESSING BIOLOGICAL SAMPLES

PRIORITY CLAIM

The present application claims the benefit of Provisional U.S. Patent Application 61/267,906, entitled "AN APPARATUS AND METHOD FOR PROCESSING BIOLOGICAL SAMPLES," filed Dec. 9, 2009, and incorporated herein by reference in its entirety.

TECHNICAL FIELD

The present invention relates to processing of a biological sample for e.g. histological and cytological examination. Especially, the present invention relates to the processing of a biological sample, for example a thin tissue section, using a small quantity of a processing fluid.

BACKGROUND OF THE INVENTION

Sample processing in immunohistochemical (IHC) applications, for example, and in other chemical and biological analyses may involve one or a number of various processing sequences or treatment protocols as part of an analysis of one or more samples. Typically, such treatment protocols are defined by organizations or individuals requesting analysis, such as pathologists or histologists working at a hospital, and may be further defined by the dictates of a particular analysis to be performed.

An in-situ hybridization (ISH) procedure, e.g. a fluorescence in-situ hybridisation (FISH) procedure, is traditionally a two day long manual procedure. Attempts have been made to automate parts of the procedure in order to shorten the processing procedure and to reduce the number of manual steps. For example, the first day pre-treatment procedure has been automated with an instrument VP2000™ (Vysis, Abbott Molecular), in which instrument a robot moves slides from one jar to another.

However, the problem so far has been to combine the pre-treatment steps of the first day and the washing steps of the second day with the strict physical and environmental requirements of the denaturation and hybridization steps in between. In these steps it is preferred to use small volumes of processing fluids and provide a precise control of the humidity in the processing chamber surrounding the processed tissue section, and to provide controlled heating and cooling in order to obtain consistent FISH results.

Automated IHC and ISH staining instruments have been introduced by Ventana Medical Systems Inc. (BenchMark™ and Discovery™) and VisionBiosystem (Bond™). A drawback with these instruments is that they only provide a fixed processing volume, i.e. the processing chamber is of a fixed volume. The processing chamber volume in the instrument is at least 100 micro liters.

The BenchMark™ instrument needs to cover the tissue section to be processed and the applied processing fluid with oil in order to reduce evaporation of the processing fluid. If not covered by oil, the evaporation of processing fluid will deteriorate the processing result.

The Bond™ instrument has a small processing chamber which is manually clamped over each tissue section and each carrier. By manually clamping the processing chamber over each carrier, an individual staining cavity is created.

In the PCT publication WO 2009/086048 A1, to Ventana Medical Systems Inc., capillary-gap-variance liquid application and removal is disclosed. One drawback to this system is that it requires a relatively complex mechanical apparatus including a motor for a each station and each station processes only one slide at a time.

In the PCT publication WO 2009/074154 A2, to Dako Denmark A/S, an apparatus for processing a biological sample arranged on a first planar surface of a carrier is disclosed. The apparatus comprises a second planar surface arranged substantially parallel to said first planar surface and at a first distance from said first planar surface, said first planar surface and said second planar surface are arranged at an angle greater than zero degrees from the horizontal plane; supply means for supplying an amount of a liquid that is to be applied to said biological sample. The first planar surface and said second planar surface are configured to be arranged at a second distance from each other, said second distance being such that said supplied amount of liquid is distributed over said biological sample when said first planar surface and said second planar surface are brought to said second distance from each other.

The sample processing apparatus disclosed in 2009/074154 A2 is not configured to easily allow a rack of slides to be automatically inserted, processed and removed.

U.S. Pat. No. 6,623,701 B1, to Max-Planck Gesellschaft zur Forderung der Wissenschaften e.V., discloses a specimen chamber for the liquid treatment of at least one specimen. The chamber comprises a base plate and a carrier plate, between which a gap-formed accommodation space is formed for the specimen, whereby the base plate and carrier plate are held together with a clamping device in a frame arrangement, and in order to form the accommodation chamber they are separated from one another by spacer elements.

A drawback with the specimen chamber of U.S. Pat. No. 6,623,701 B1 is that each specimen chamber has to be manually assembled before the processing of a specimen can be started. To manually assembly the chamber requires several steps and the associated time and work for each step and requires some skills of the person assembling the chamber in order to get the parts of the chamber to be arranged in their correct position. This manual assembly process with many steps increases the opportunity for human errors.

The PCT publication WO 2006/116037, to Celerus Diagnostics Inc., discloses a sample processing system that may be configured to achieve rapid sample processing such as rapid histochemical processing. The processing system may involve a wave element that can use angular microscopic slide movements to cause repeated elimination and reapplication of a fluidic substance perhaps through the action of capillary motion in order to refresh a microenvironment adjacent to a sample such as a biopsy or other such sample. Through such refreshing of a microenvironment, depletion of the microenvironment is avoided and the time necessary for slide processing may be shortened.

Drawbacks with the sample processing system disclosed in WO 2006/116037 are that a confined fluidic environment around a sample on a slide is accomplished by using an opposing slide that in one end is hinged to one end of the slide carrying the sample causing. As with the other systems, multiple slides in a single rack cannot be automatically loaded and unloaded into the processing location. Further, this system utilizes a wicking mechanism in the form of a large cartridge of absorbable material, thus increasing the operational cost of the instrument.

Further, mixing of the fluid within the confined fluidic environment is accomplished by providing an angled movement of the opposing slide, i.e. by rotating the opposing slide around the hinge.

Some of the drawbacks with prior art instruments are that they require relatively large volumes, about 150-200 micro liters, of processing fluid, that they do not provide as good results as manual processing, that they do not automatically provide a processing chamber and that they do not provide a variable volume of processing fluid to be used by providing a processing chamber having a variable volume. Further many of the prior art instruments are relatively complex requiring a large number of moving parts. Further, the prior art instruments often require manual assembly or attachment of a cover or lid to form a capillary gap or they require an evaporation preventing liquid to be applied on a pool of processing reagent during incubation which typically results in a higher volume of reagent needing to be applied.

An aim of the present invention is to solve these and other problems and drawbacks with the prior art system. For example, an object of the present invention is overcome the drawback of having a complex mechanism that processes only one slide at a time.

Another object of the present invention is to overcome the drawbacks of horizontal carrier systems that require a vacuum to evacuate the capillary chamber.

Yet another object of the present invention is to solve the problem of having a fixed volume of processing fluid or of requiring a relatively large amount of processing fluid for automated protocols compared to the amount of fluid required for manual protocols of the same type.

Another object of the invention is to eliminate the problem of requiring separate complex mechanisms for mixing of a fluid on each single slide.

SUMMARY OF THE INVENTION

The present invention concerns molecular pathology, i.e. the examination at a molecular level of the DNA; mRNA, and proteins that cause or are otherwise associated with disease. The present invention relates to processing of a biological sample for e.g. histological and cytological examination. Especially the present invention relates to the processing of a thin biological sample, e.g. a tissue section, using a small quantity of a processing fluid.

In particular, the invention relates to processing, e.g. treating and/or staining, of at least one biological sample, e.g. a tissue section, accommodated on a carrier as well as to the control of the humidity and temperature during the processing.

It should be understood that the present invention may be used in the fields of cytology and histology, molecular biology, biochemistry, immunology, microbiology, and cell biology. In particular, the invention relates to the fields of molecular cytogenetics and immunohistochemistry, for processing biological samples in immunohistochemistry (IHC), in-situ hybridization (ISH), fluorescent in-situ hybridization (FISH), chromogenic in-situ hybridization (CISH), special stains (SS), silver in-situ hybridization (SISH), microarrays (tissue, protein, RNA, DNA, PNA, LNA, etc.) as well as other chemical and/or biological applications.

Immunologic applications, for example, may involve processing sequences or protocols that comprise steps such as deparaffinization, target retrieval, and staining, especially for in-situ hybridization (ISH) techniques.

The staining procedure may be laborious and use many different kind of liquids, e.g. reagents. The staining protocol may include the following steps: deparaffinization, washing, antigen retrieval, endogenous biotin or enzyme blocking, incubation with immunological reagents, molecular probes, secondary visualization reagents and various chromogen reagents, washing steps and counterstaining.

The present invention relates to an automated staining apparatus for processing at least one biological sample arranged on a slide. Embodiments of the automated staining apparatus comprise:
   at least one capillary staining module comprising:
      a slide rack holder configured to detachably hold a slide rack configured to hold one or more slides, and
      a capillary lid rack holder configured to detachably hold a capillary lid rack configured to hold one or more capillary lids, wherein the slide rack can be removed independently of removing the capillary lid rack, and
   a first fluid container comprising a first fluid,
wherein the automated staining apparatus is configured to automatically:
   control the slide rack holder to rotate the one or more slides from an insert position to one or more inclined positions, and to control the capillary lid rack holder to move the one or more capillary lids towards the one or more slides to automatically form a capillary gap between each slide and each capillary lid, said capillary gap functioning as a capillary chamber; and to
   supply an amount of the first fluid from the fluid container to the slide when in said inclined position.

The present invention also relates to an automated method for processing at least one biological sample arranged on a slide, embodiments of the method comprise:
   providing at least one capillary staining module comprising:
      a slide rack holder configured to detachably hold a slide rack configured to hold one or more slides, and
      a capillary lid rack holder configured to detachably hold a capillary lid rack configured to hold one or more capillary lids, wherein the slide rack can be removed independently of removing the capillary lid rack,
   providing a first fluid container comprising a first fluid,
   automatically controlling the slide rack holder to rotate the one or more slides from an insert position to one or more inclined positions;
   automatically controlling the capillary lid rack holder to move the one or more capillary lids towards the one or more slides to automatically form a capillary gap between each slide and each capillary lid, said capillary gap functioning as a capillary chamber; and
   automatically supplying an amount of the first fluid from the fluid container to the slide when in said inclined position.

Preferred embodiments of the invention are defined in the dependent claims.

DETAILED DESCRIPTION OF THE DRAWINGS

The objects, advantages and effects as well as features of the present invention will be more readily understood from the following detailed description of embodiments of the invention, when read together with the accompanying drawings, in which:

FIG. 1A is an oblique schematic illustration of an embodiment of an automated staining apparatus comprising an IHC automated capillary staining module and an ISH automated capillary staining module;

FIG. 1B schematically illustrates a biological sample arranged on a slide;

Figure 3A:
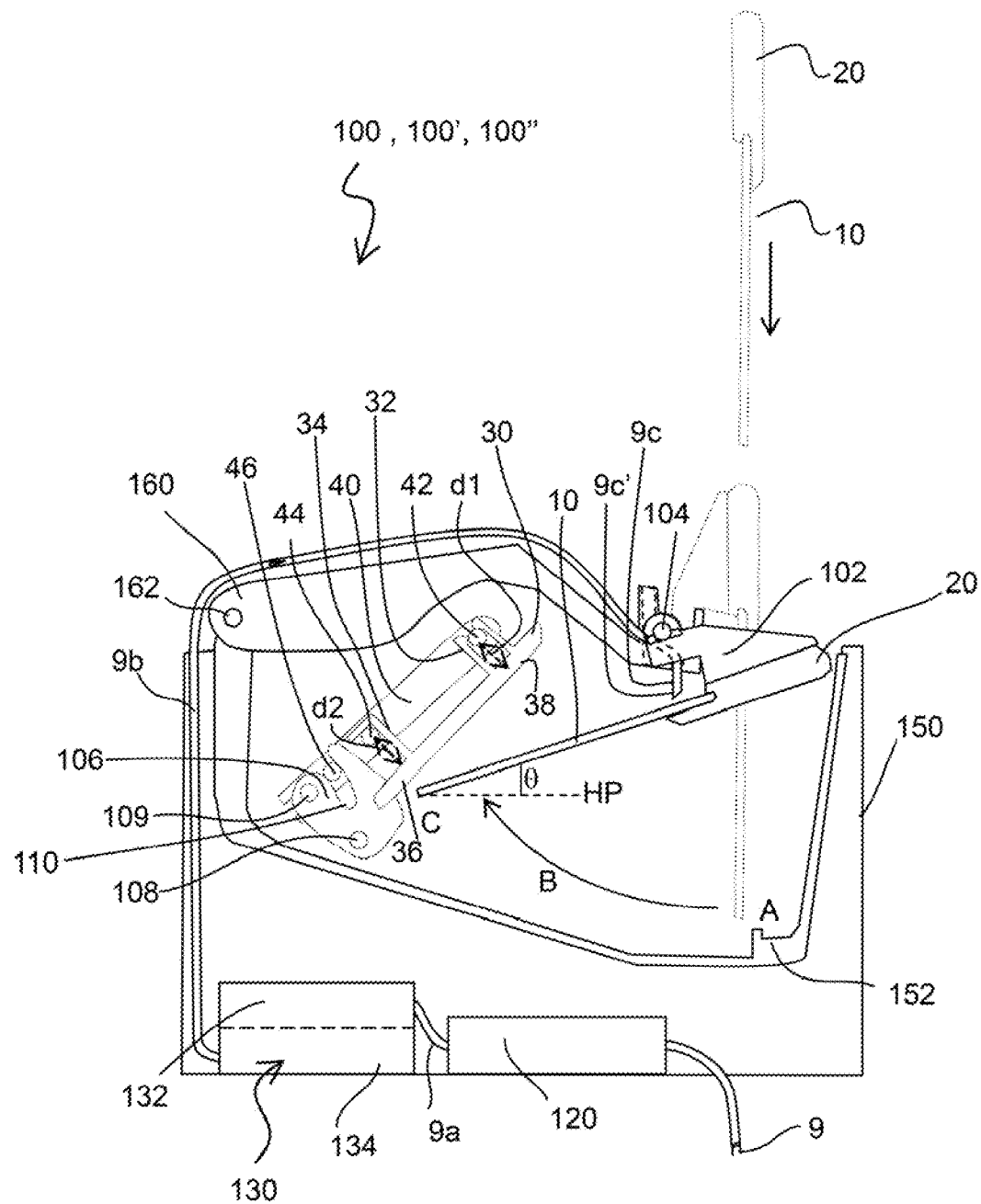
Figure 3B:
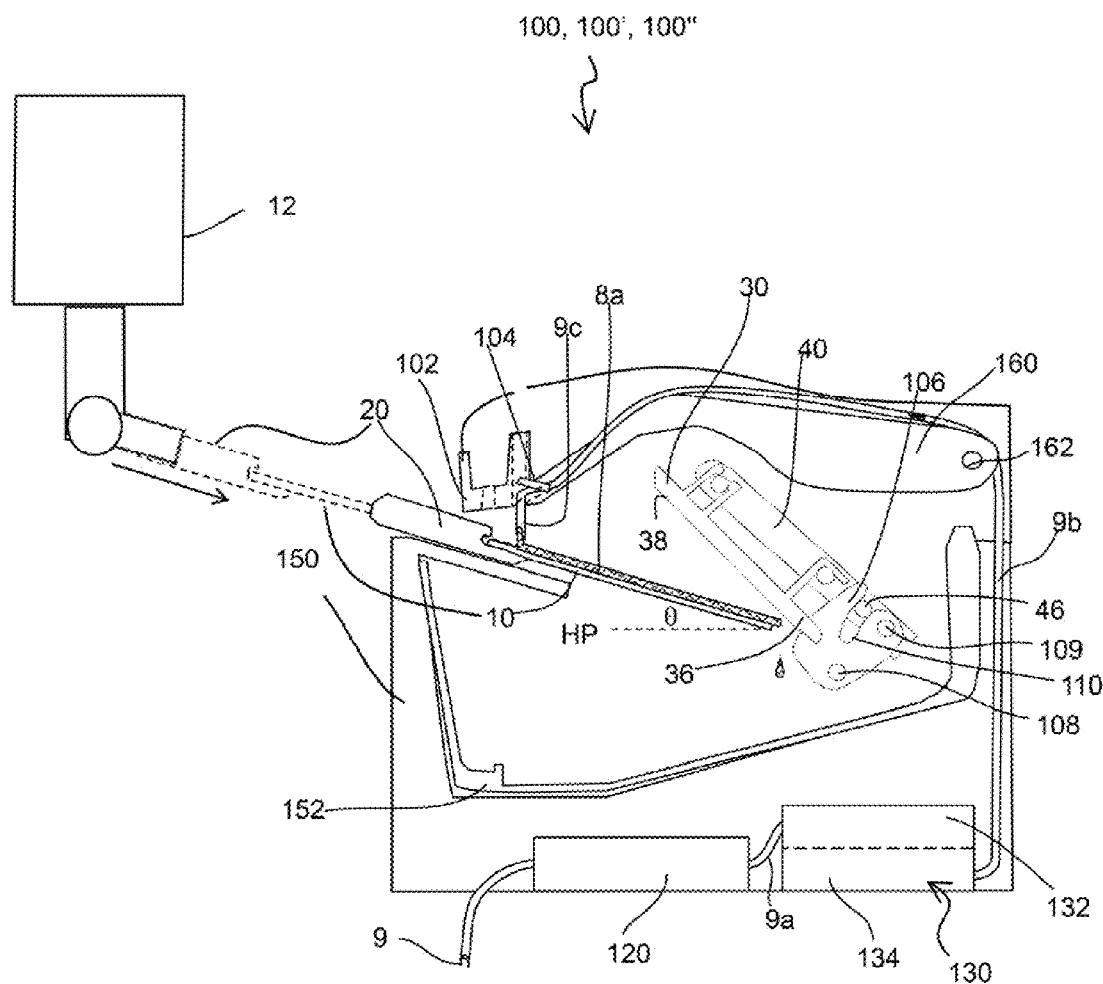
Figure 4:
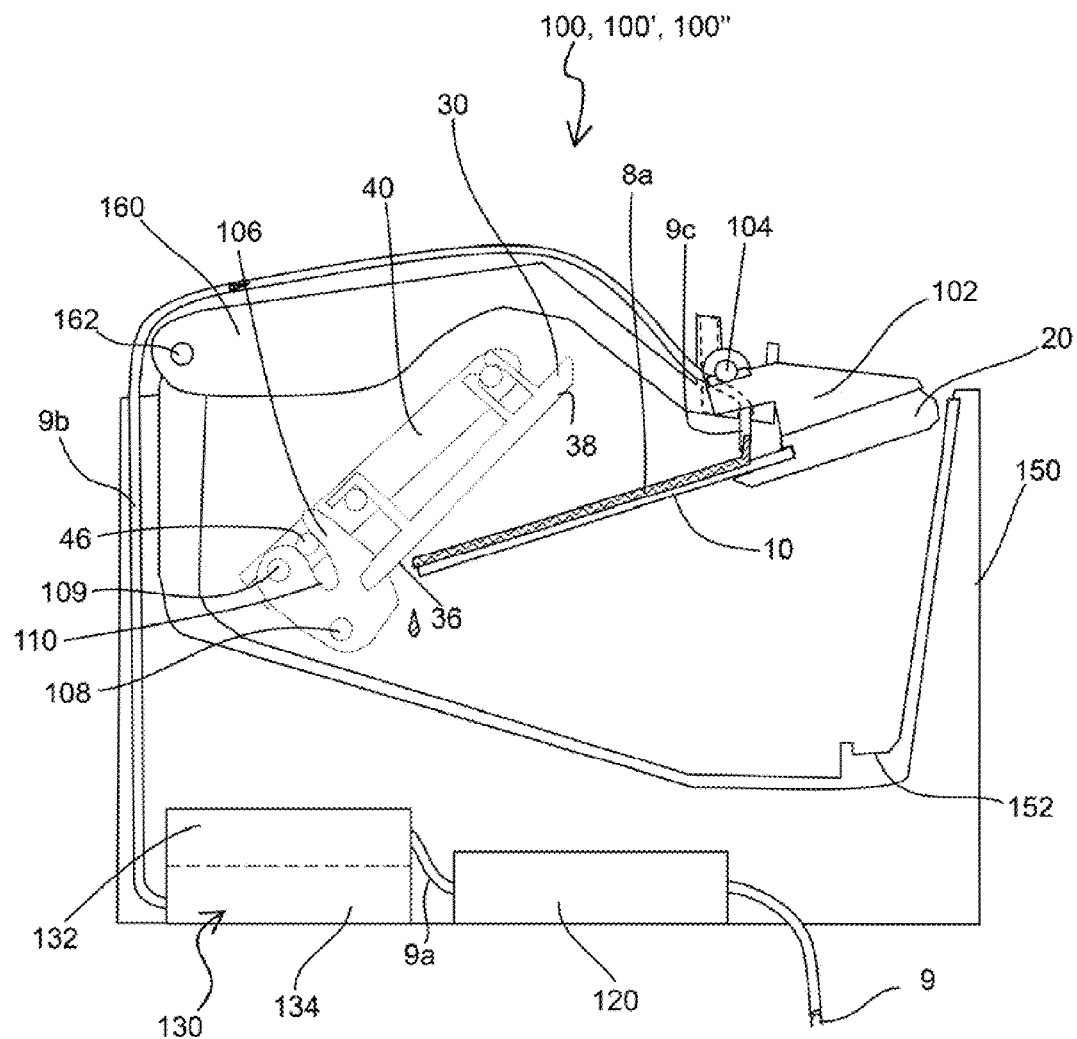
Figure 5:
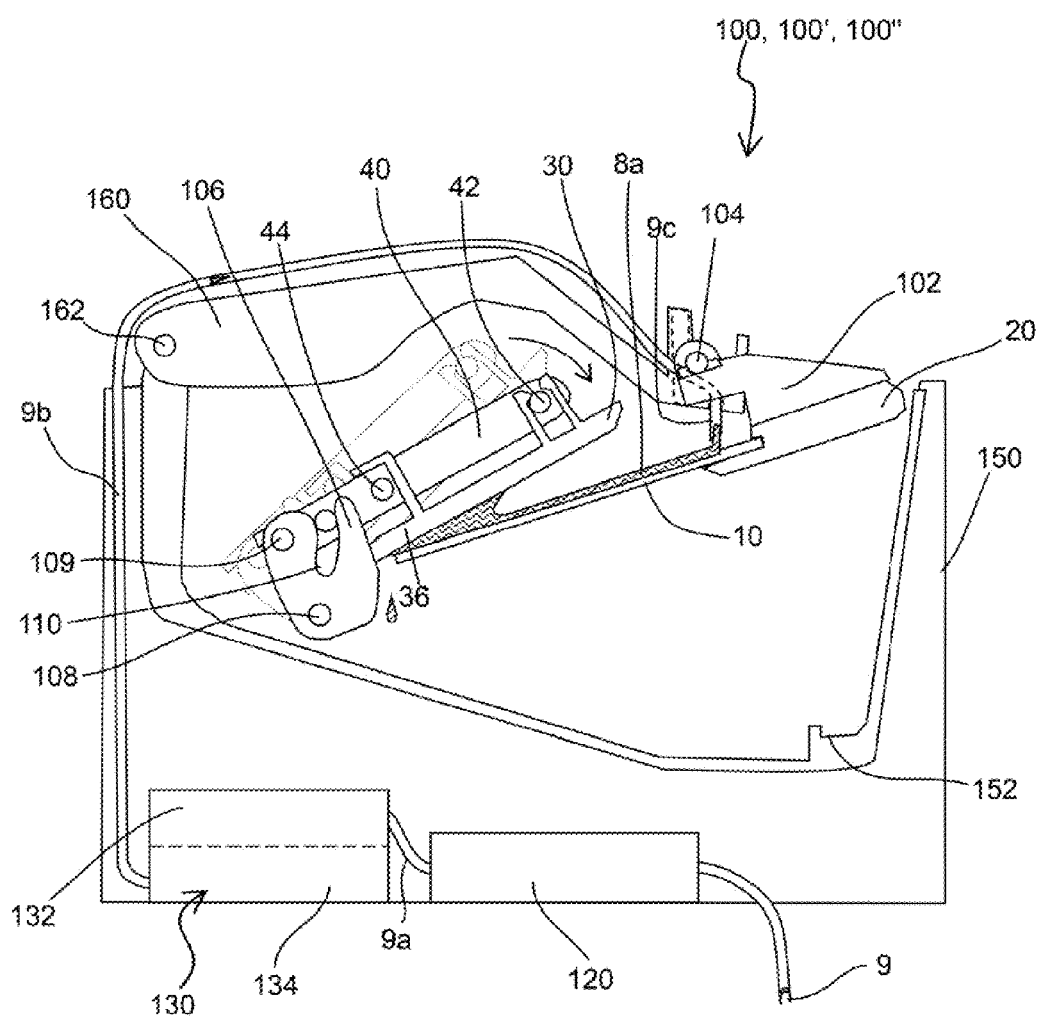
Figure 6:
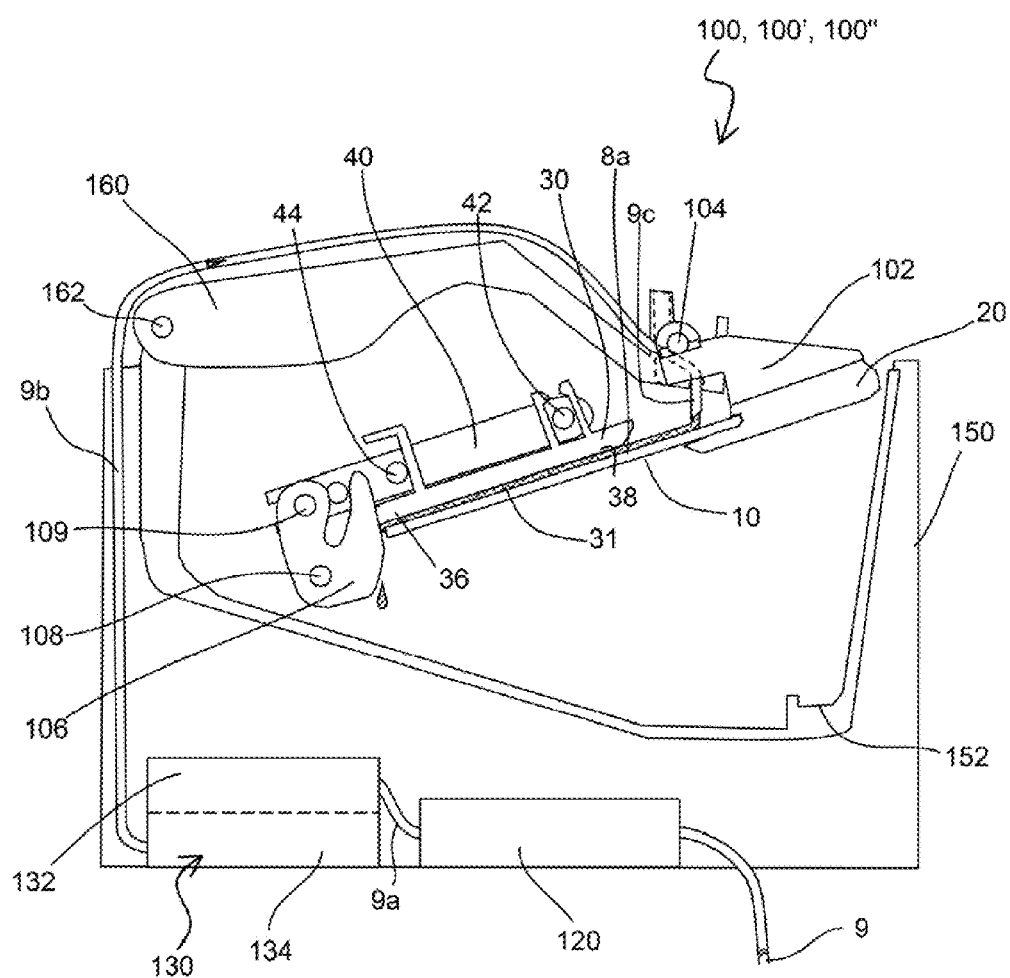
Figure 7:
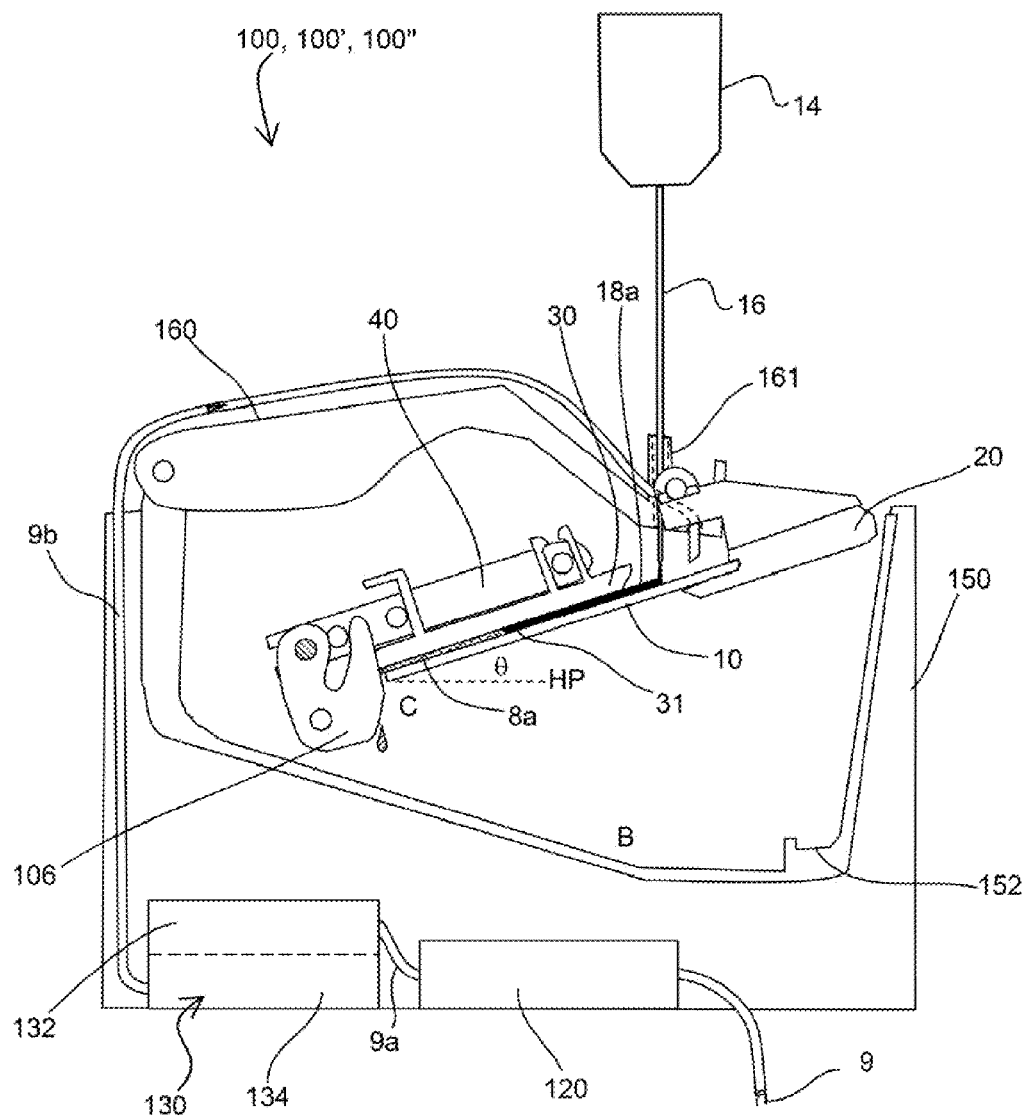
Figure 8:
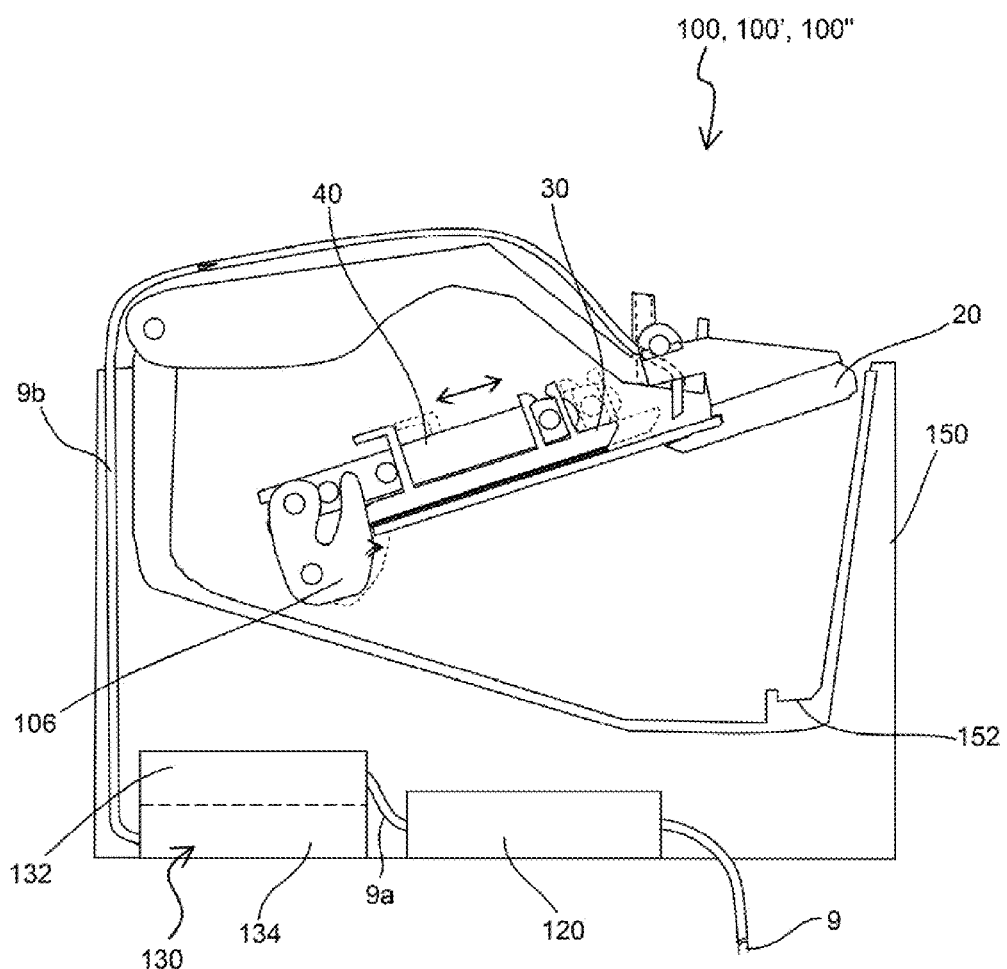
Figure 9:
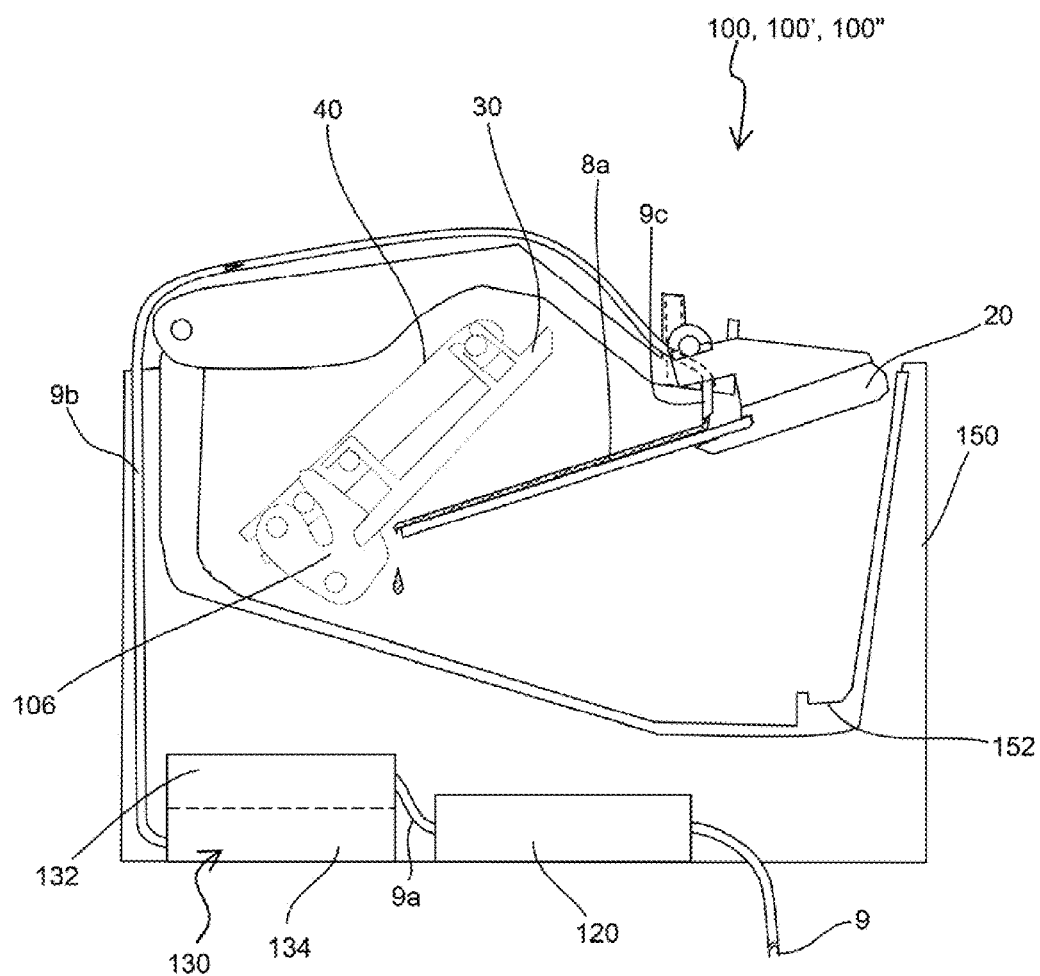
Figure 10:
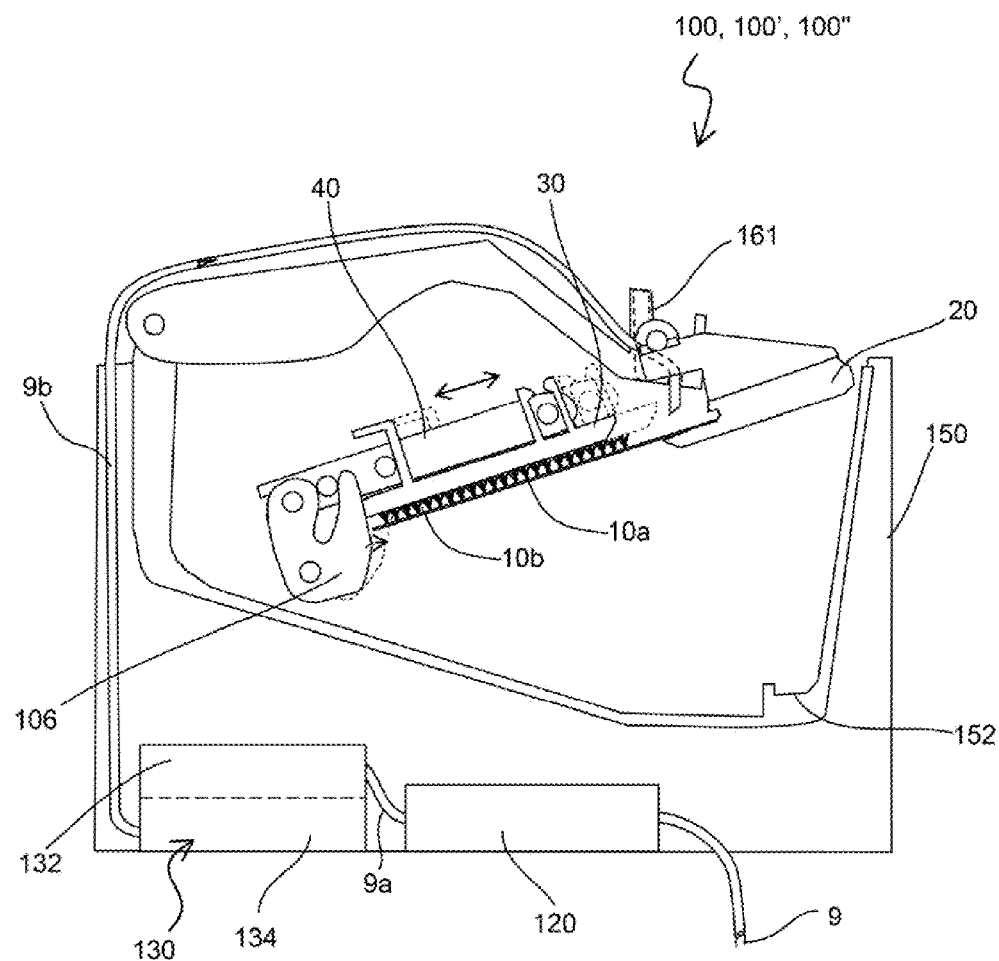
Figure 11:
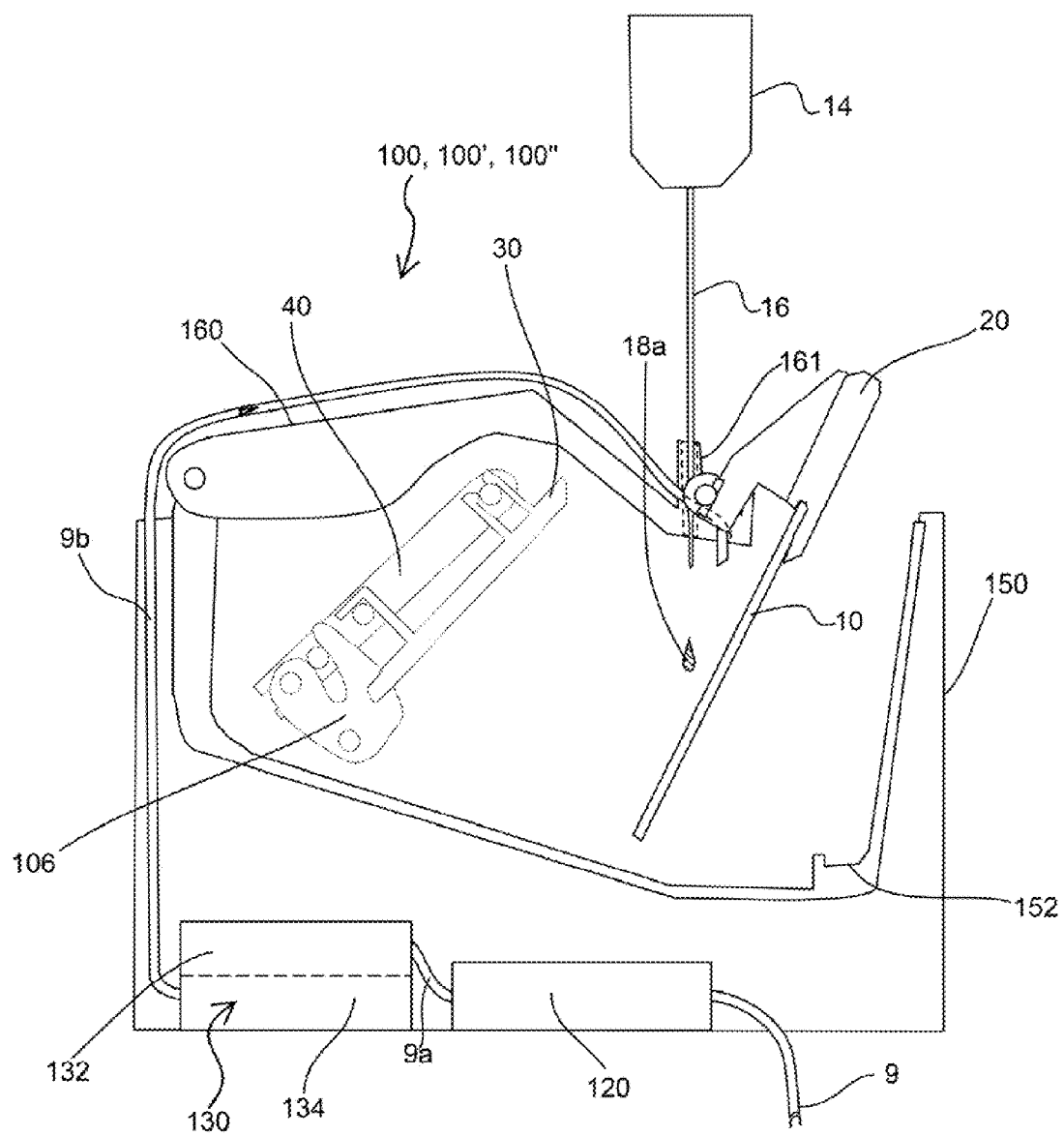
Figure 12:
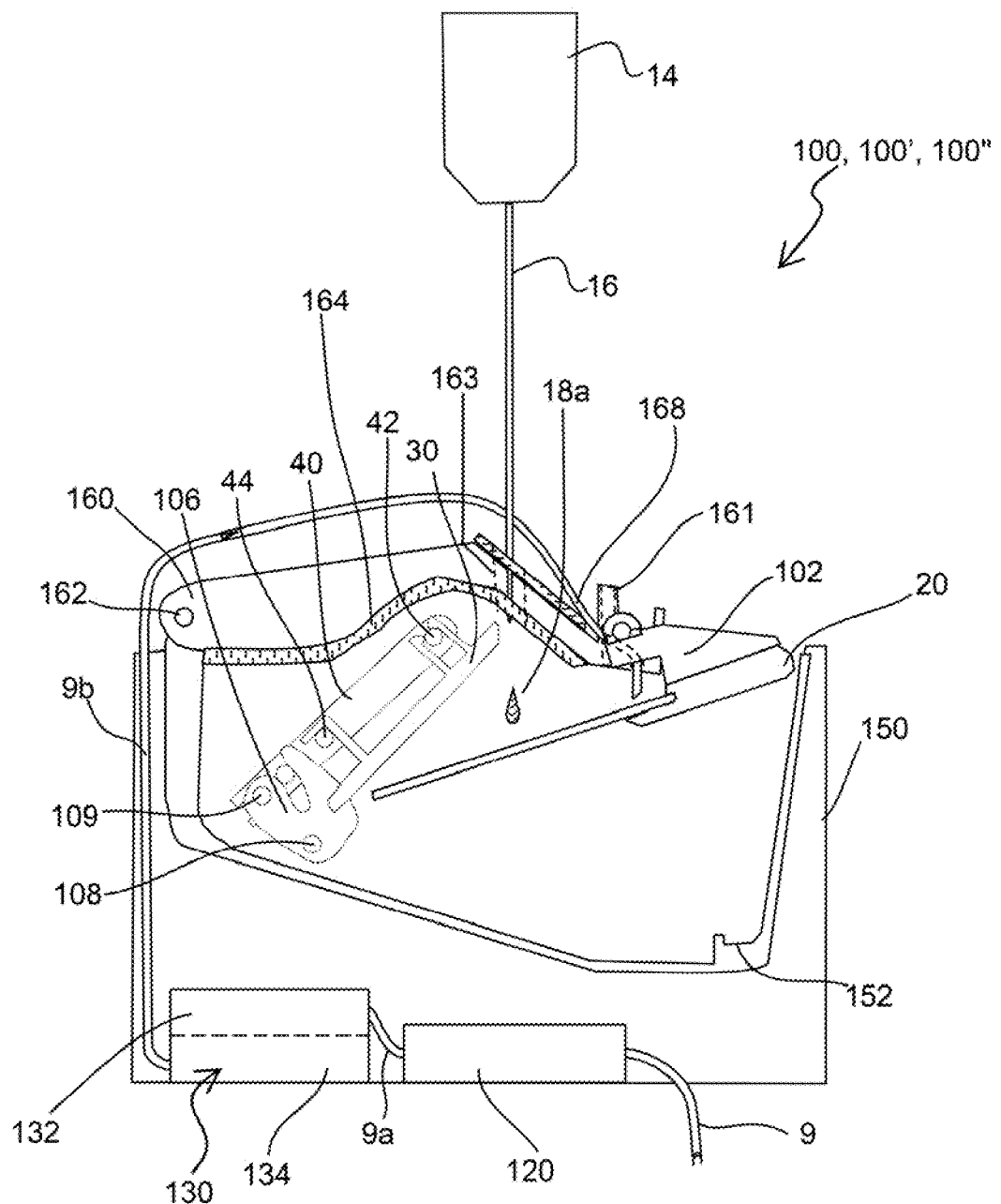
Figure 13:
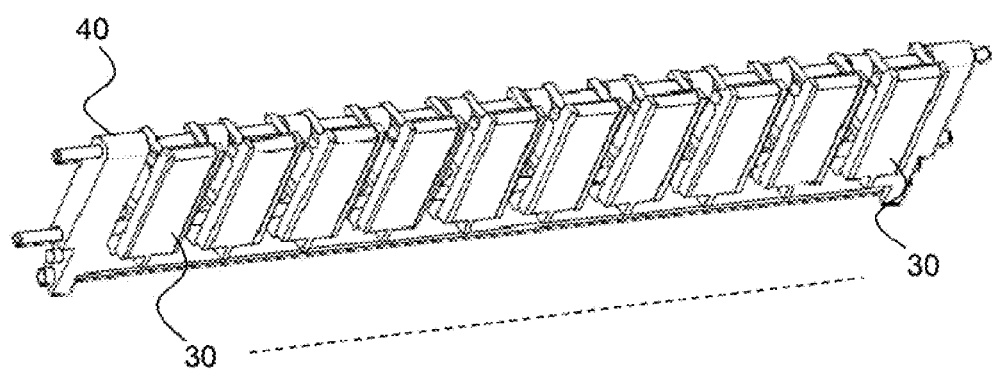
Figure 14A:
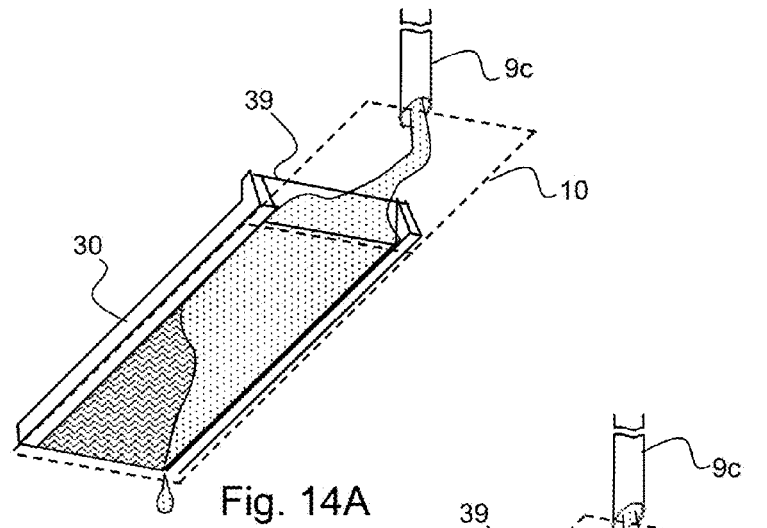
Figure 14B:
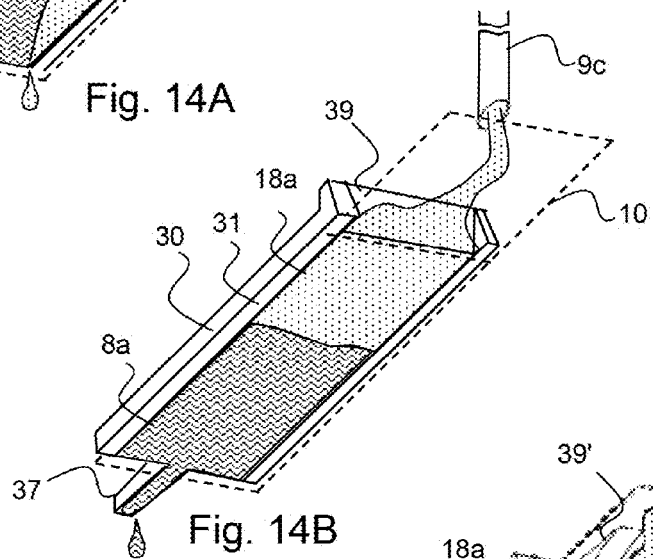
Figure 14C:
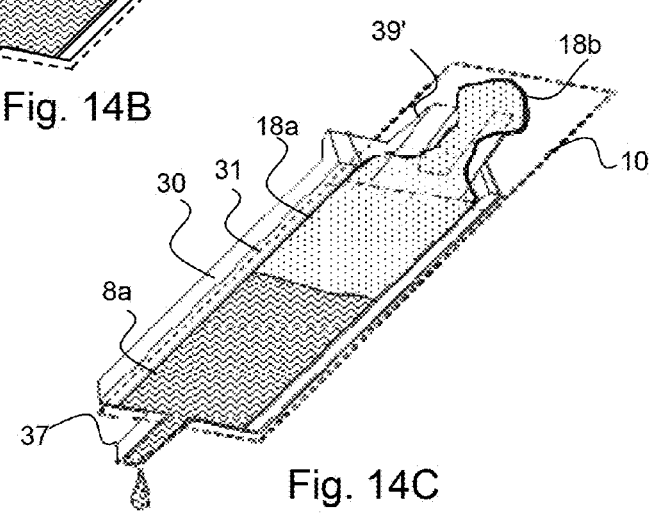
Figure 15A:
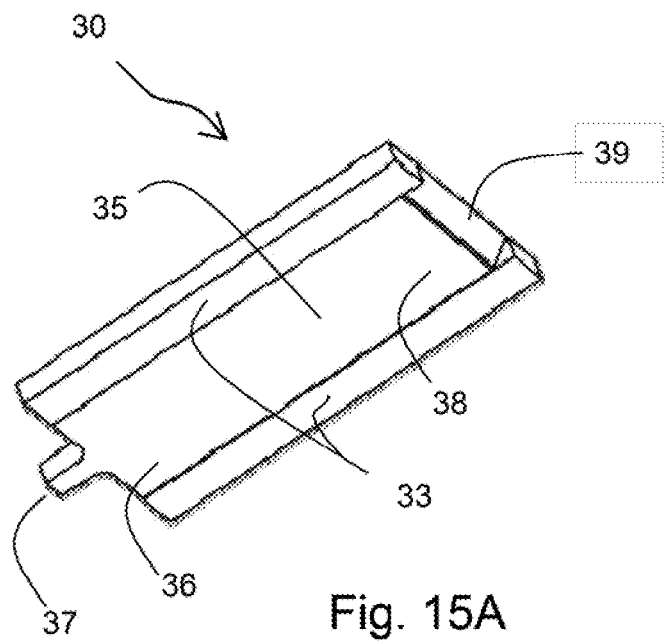
Figure 15B:
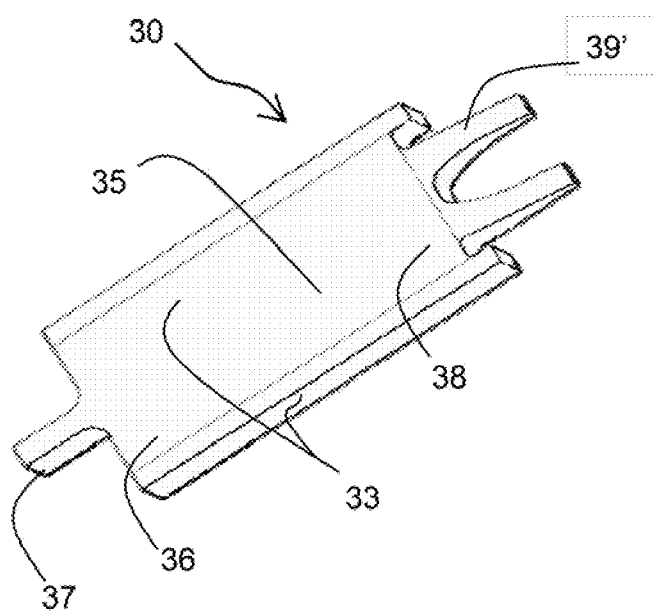
Figure 16A:
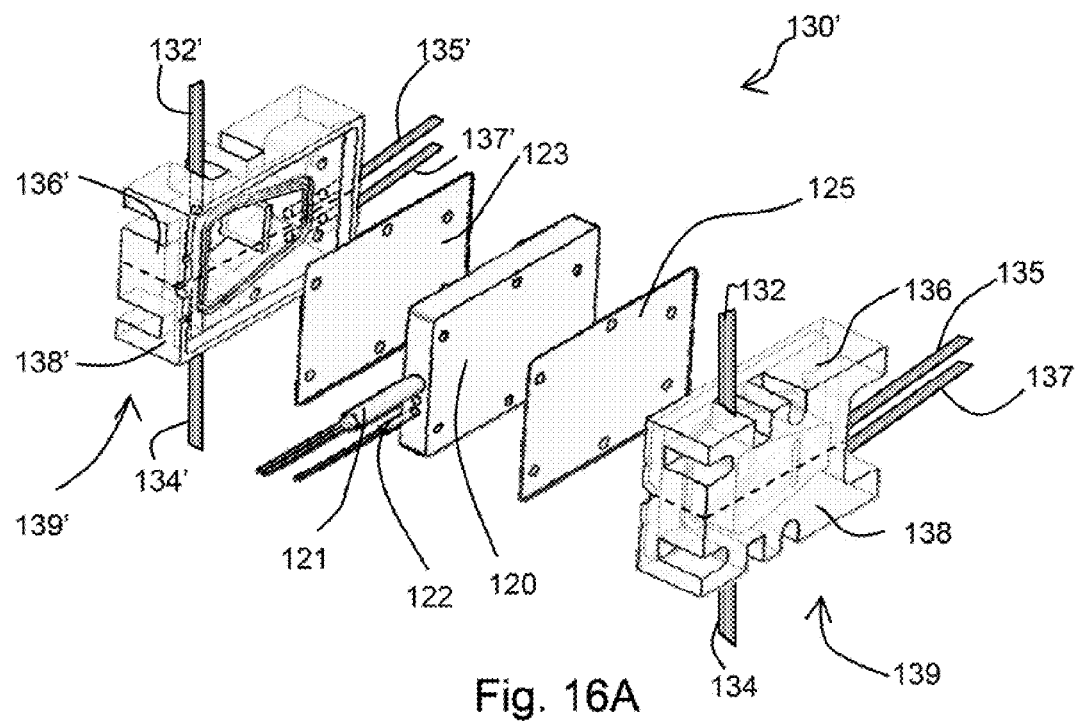
Figure 16B:
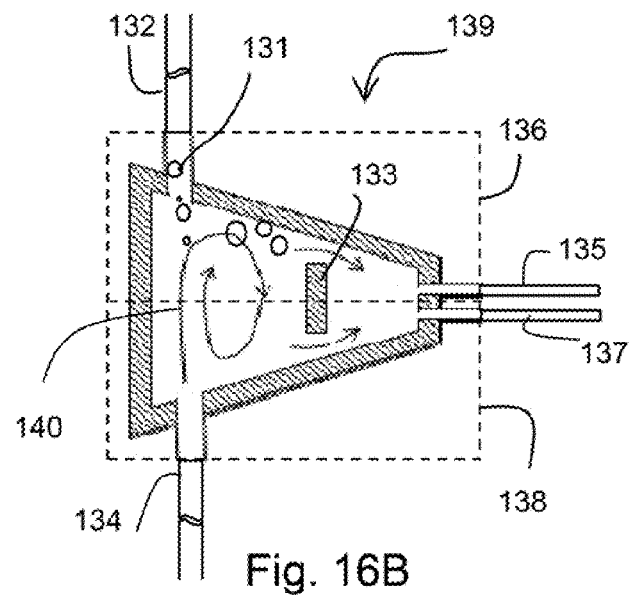

FIG. 3A schematically illustrates a cross-sectional view of an embodiment of the capillary staining module in which vertical slide rack insertion followed by rotation is shown;

FIG. 3B schematically illustrates across-sectional view of another embodiment of the capillary staining module in which inclined slide rack insertion without rotation is shown;

FIG. 4 schematically illustrates a cross-sectional view of an embodiment of the capillary staining module in which initial fluid supply to a slide in an inclined position is shown;

FIG. 5 schematically illustrates a cross-sectional view of an embodiment of the capillary staining module in which capillary lid rack rotation is shown;

FIG. 6 schematically illustrates a cross-sectional view of an embodiment of the capillary staining module in which a fluid filled capillary gap is obtained between a capillary lid and a slide;

FIG. 7 schematically illustrates a cross-sectional view of an embodiment of the capillary staining module in which an amount of a reagent is supplied to the fluid filled capillary gap;

FIG. 8 schematically illustrates a cross-sectional view of an embodiment of the capillary staining module in which the capillary lid performs an oscillating movement;

FIG. 9 schematically illustrates a cross-sectional view of an embodiment of the capillary staining module in which the capillary gap between a capillary lid and a slide is removed during fluid supply;

FIG. 10 schematically illustrates a cross-sectional view of an embodiment of the capillary staining module in which a capillary lid is cleaned by means of a cleaner-type slide;

FIG. 11 schematically illustrates a cross-sectional view of an embodiment of the capillary staining module in which in which a reagent is dispensed;

FIG. 12 schematically illustrates a cross-sectional view of an embodiment of the capillary staining module comprising condensation preventive means, in which a reagent is dispensed;

FIG. 13 schematically illustrates an embodiment of a capillary lid rack comprising ten capillary lids;

FIG. 14A schematically illustrates fluid flow in a capillary gap between a slide and a capillary lid without a drip tip;

FIG. 14B schematically illustrates fluid flow in a capillary gap between a slide and a capillary lid with a drip tip;

FIG. 14C schematically illustrates fluid flow in a capillary gap between a slide and a capillary lid with a drip tip and a droplet catcher;

FIG. 15A schematically illustrates an embodiment of a capillary lid comprising spacers, a central recess, a drip tip, and a chamfered upper end;

FIG. 15B schematically illustrates an embodiment of a capillary lid comprising spacers, a central recess, a drip tip, and a chamfered upper end with a droplet drainer;

FIG. 16A is an exploded oblique view of an embodiment of an bubble trap combined with an in-line fluid heater; and FIG. 16B schematically illustrates an embodiment of a bubble trap and the flow of fluid and bubbles within the bubble trap.

DETAILED DESCRIPTION OF THE INVENTION

While the invention covers various modifications and alternative methods, apparatuses and systems, embodiments of the invention are shown in the drawings and will hereinafter be described in detail. However, it is to be understood that the specific description and drawings are not intended to limit the invention to the specific forms disclosed. On the contrary, the scope of the claimed invention is intended to include all modifications and alternative constructions thereof falling within the spirit and scope of the invention as expressed in the appended claims to the full range of their equivalents. In the drawings, the same reference numeral is used for the same or similar feature.

Figure 1A:
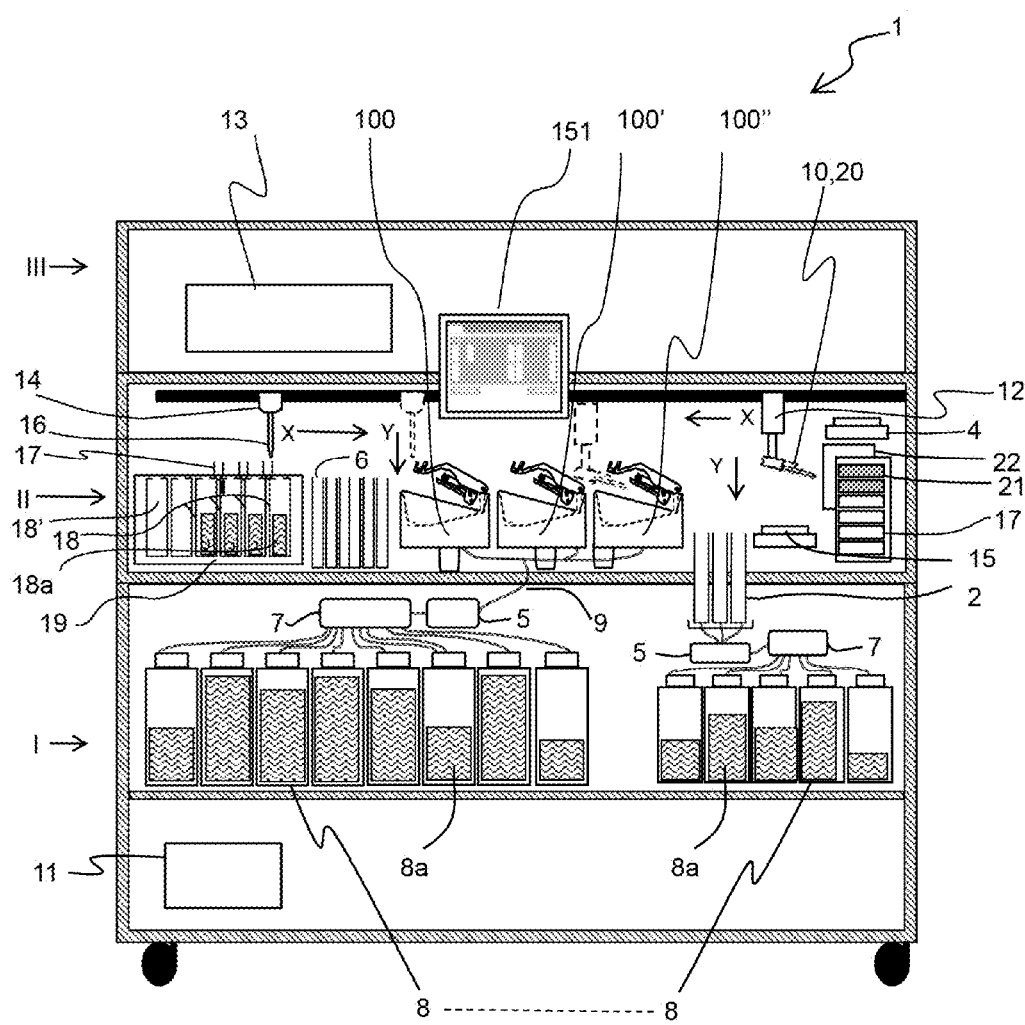
FIG. 1C is an oblique view of upper and middle sections of an embodiment of an automated staining apparatus comprising an automated capillary staining module.
Figure 1B:
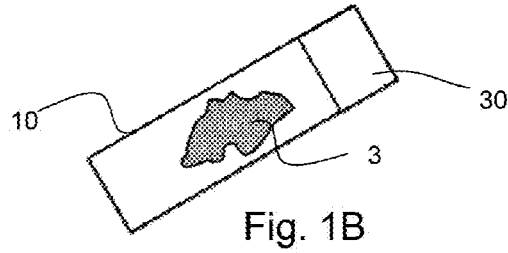

In an embodiment of the invention and as schematically illustrated in FIG. 1A, an automated sample processing apparatus 1, in this description also referred to as an automated staining apparatus 1, comprises at least one capillary processing module 100, in this description also referred to as a capillary staining module 100, for processing at least one biological sample 3, such as a biological tissue sample, arranged on a sample holder 10, cf. FIG. 1B.

The biological sample may be presented on the sample holder variously and potentially in some form of preservation. As one example, a sample such as a layer or slice of skin, tumor, or other tissue may be preserved in formaldehyde and presented on a sample holder with one or more paraffin or other chemical layers overlying the sample. Samples preserved with paraffin may need to undergo deparaffinization, a process by which paraffin layers overlaying and/or infiltrating the sample are removed. In addition, the target or sample may need to be restored to a condition where it is suitable for staining operations—a process known as target retrieval.

As used herein, automated is defined as a plurality of steps that are executed by substantially mechanical, computer and/or electronic means. It does not exclude some human intervention steps such as manually replacing one of the described features or steps.

Even though, in this description, reference is made to a slide it should be understood that slide refers to a sample holder, and the sample holder is any medium that supports a sample. Thus, sample holder includes any support, such as a carrier, test tube, chip, array, disk, or slide that can support at least one sample.

Further, in this description reference is also made to a slide rack. However, slide rack should be understood to include any suitable holder for a group of supports such as a rack supporting a group of slides. Slide rack may further refer to a larger scale support, such as a slide rack holder that holds at least one smaller support, such as a plurality of slide racks, each rack containing a plurality of slides. A holder may releasable hold, securely hold, and/or hold in such a way that permits movement, such as vertical, horizontal or pivoting about one or more axis.

As schematically illustrated in FIG. 1A, the automated staining apparatus 1 comprises a first capillary staining module 100, a second capillary staining module 100', and a third capillary staining module 100", but it should be understood that the number of capillary staining modules can be varied.

In embodiments, the first, second, and third capillary staining modules, 100, 100', and 100" may be configured for e.g. immunohistochemical (IHC) applications, and in-situ hybridisation (ISH) applications, respectively.

As schematically illustrated in FIG. 1A, the staining apparatus 1 may comprise three levels; a first, lower, level I comprising e.g. bulk fluid containers, waste, valves and pumps; a second, middle, level II comprising e.g. a number of processing units, slide storages, robotics and reagent vials; and a third, upper, level III comprising e.g. a cover slipper and control units and communication interfaces. Certain elements such as control unit 151 may be positionable to level III to roughly enable an eye-level view of the display, or to level I to be out of the way when manually accessing the modules in level II.

As illustrated, the automated staining apparatus 1 may comprise one or more processing units, such as one or more pretreatment modules 2, sometimes referred to as dip tanks, slide storage units 6 and one or more capillary staining modules 100, 100', 100".

In embodiments, a pretreatment module 2 may be configured for deparaffinization, i.e. for removal of paraffin from a paraffin-embedded biological sample. Pretreatment module 2 may also be configured for target retrieval (e.g., antigen retrieval, or in-situ hybridization), i.e. for restoring the target/antigen of the sample to a condition where it is suitable for staining operations.

Automated staining apparatus 1 may include sample loading stations 17 for inserting slide racks with samples into the apparatus for processing. Automated staining apparatus 1 may further include accessory loading stations 21 for inserting accessories such as lids for in-situ hybridization protocols.

The one or more slide storage units 6 are configured to store one or more slides 10 arranged on one or more slide racks 20 configured to hold a number of slides 10 mounted side by side. The slide storage units 6 are configured to store slides horizontally, vertically, or in another suitable position.

The automated staining apparatus 1 may further comprise a number of containers 8 of bulk fluids 8a, such as washing solutions, buffer solutions, deparaffinization solutions, target retrieval solutions or aqueous solutions, such as purified water, antibodies in solution, bulk staining solutions such as hematoxylin, eosin, cleaning solutions such as DAB removing solution, etc. known to a person skilled in the art.

The automated staining apparatus 1 may further comprise tubings 9 connecting the bulk fluid container(s) 8 to one or more processing units 2, 100, 100', 100", valves 7 for controlling the flow of bulk fluid 8a to the one or more processing units 2, 100, 100', 100", from the bulk fluid container(s) 8, and one or more pumps 5 configured to provide a flow of bulk fluid from the bulk fluid container 8 to the one or more processing units 2, 100, 100', 100".

Further, the automated staining apparatus 1 may comprise a waste container 11 configured to store waste fluid which has been removed by tubings (not shown) from the one or more processing units 2, 100, 100', 100".

As schematically illustrated in FIG. 1A, the automated staining apparatus 1 comprises further a slide robot 12 configured to transport one or more slides 10 or one or more slide racks 20 in X and Y (as well as Z) direction as indicated by the arrows X and Y. By a slide robot 12, the slides/slide rack may be transported between different processing units 2, 100, 100', 100" and storages 6 of the staining apparatus 100 so that the biological samples arranged on the slides can be processed as desired.

In FIG. 1A, it is schematically illustrated how the slide robot 12 lifts, along the Y direction, a slide 10 or a slide rack 20 from a slide storage 6. Further, as indicated by the arrow, the slide robot 12 can move to the left, along the X direction, to for example a first capillary staining module 100, 100', 100".

Slide robot 12 may grab a slide rack 20 from sample drawer 17 and transport the slide rack 20 and slides 10 to any of the stations such as cold plate 15, hot plate 4, incubation station 22, pretreatment modules 2, staining modules 100, 100', 100", or wet/dry unload modules 6 in order to process the samples 3 upon the slides 10.

When the slide robot 12 is arranged at a position above the slide rack position of the capillary staining module, the slide robot 12 can be configured to lower, along the Y direction, the slide or slide rack into the capillary staining module to insert the slide or slide rack in a correct position within the capillary staining module, as indicated by the downwards directed arrow along the Y direction in FIG. 1A.

Further, slide robot 12 may be configured to position slide rack 20 horizontally, vertically or at an angle between horizontal and vertical. For example, slide robot 20 may grasp or release slide rack 20 in a horizontal orientation upon cold plate 15 or hot plate 4 or loading stations 17. As a further example, slide robot 12 may grasp or release slide rack 20 in a vertical orientation at pretreatment modules 2 or unloading stations 6. In yet another example slide robot 12 may grasp or release slide rack 20 in an angled orientation between horizontal and vertical such as staining modules 100, 100' and 100".

Furthermore, the automated staining apparatus 1 comprises a fluid robot 14 for moving a probe 16 in X and Y (as well as Z) direction as indicated by the arrows X and Y. The fluid robot 14 may position the probe 16 above one or more fluid containers 18, mixing stations, capillary staining modules 100, 100', 100", cold plate 15, and hot plate 4.

The fluid robot 14 may further operate the probe 16 to aspirate portions of reagent 18a contained in any of the reagent containers 18, to transfer the portion of reagent 18a and apply it to one or more slides 10 arranged in one or more of the capillary staining modules 100, 100', 100" in order to provide a selected staining or treatment of the sample on the slide. As schematically illustrated in FIG. 1A, one or more fluid containers 18 can be arranged in a fluid container rack 19.

Thus, the fluid robot 14 is configured to move the probe 16 between different positions within the automated staining apparatus 1. The fluid robot 14 may for example be configured to move the probe 16 to e.g. an aspiration position at a reagent container 18 and to let the probe 16 aspirate an amount of a reagent 18a from the reagent container 18. Further, as schematically illustrated by the leftward directed arrow, along the X direction, and the downward directed arrow, along the Y direction, by fluid robot 14, the probe 16 can be moved to e.g. a dispensing position at a slide 10 arranged in a capillary staining module 100, 100', 100", at which dispensing position, a volume of the aspirated reagent 18a can be dispensed to the slide 10 in order to provide a selected staining or treatment of the sample on the slide.

As schematically illustrated in e.g. FIGS. 7, 11, and 12, the dispensing position can be defined by a first probe inlet 161 and/or a second probe inlet 163, respectively, arranged in a processing container lid 160.

However, it should be understood that the number of first and second probe inlets 161, 163, can be varied and that, in embodiments, the number of first and second probe inlets 161, 163 are equal to the number of slides that can be processed in the capillary staining module. Thus, in embodiments, in the processing container lid 160, a first and a second probe inlet 161,163 is arranged for each slide that can be processed in the capillary staining module in order to provide individual supply of fluid to each slide.

Further, the automatically created capillary chamber as described herein may be used in conjunction with fluid dispensing mechanisms including robotic pipettes, probes, tubes, direct dispensing bottles, manifolds, and so forth.

Before aspirating an amount of a possible different second fluid, the probe 16 can be moved to a washing fluid container 18' and an amount of the washing fluid can be aspirated in order to clean the probe 16 before an amount of a possible new fluid is aspirated by the probe 16.

As schematically illustrated in FIG. 1A, the one or more reagent containers 18, 18' can be arranged in a reagent container rack 19. A plurality of reagent container racks may be configured to be independently insertable and or removable in order to accommodate continuous workflow, i.e. adding or removing reagents during ongoing processing of slides.

Further, the automated staining apparatus 1, may further comprise a cover slipper 13 configured to arrange a cover glass (not shown) on a processed biological sample arranged on a slide 10.

As schematically illustrated in FIG. 1A, the automated staining apparatus 1 may also comprise a control unit 151 comprising processing control and an input/output interface. A suitable input can be a keyboard and a suitable output can be a monitor or control unit 151 may comprise a touch screen display.

Figure 1C:
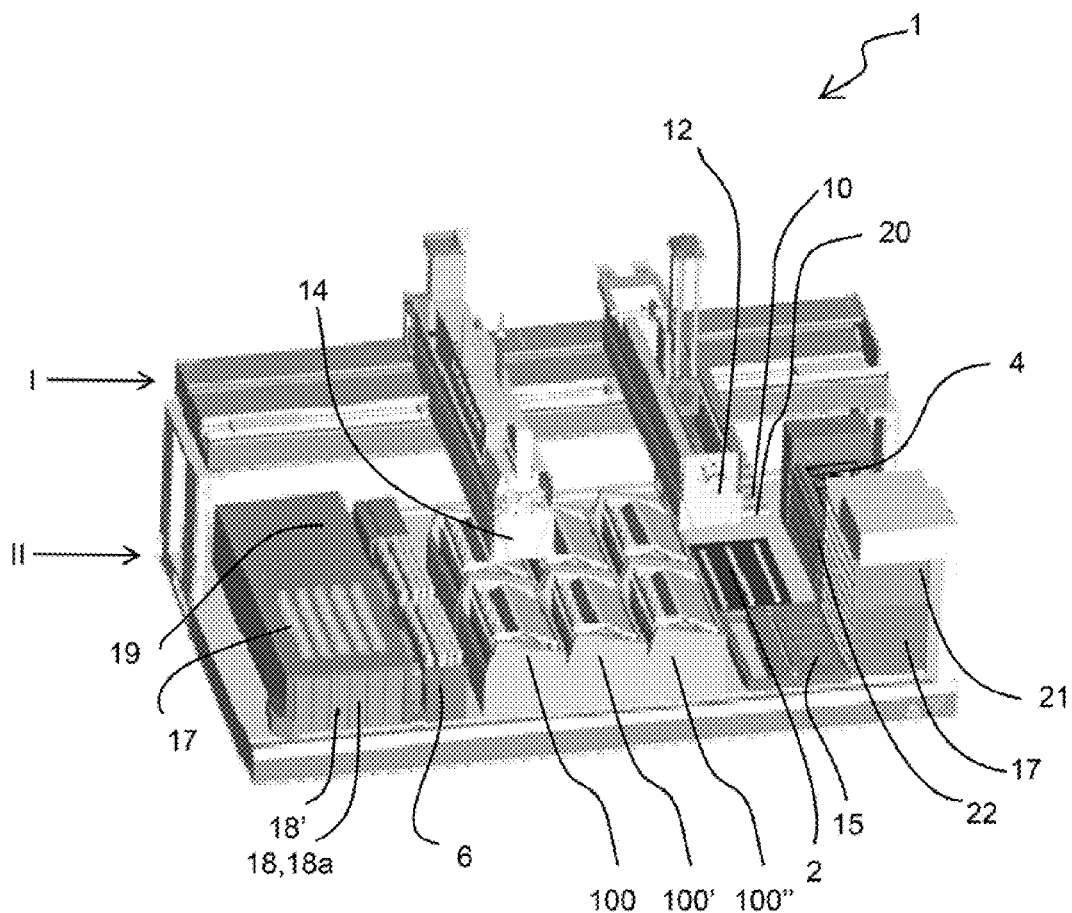
Figure 2A:
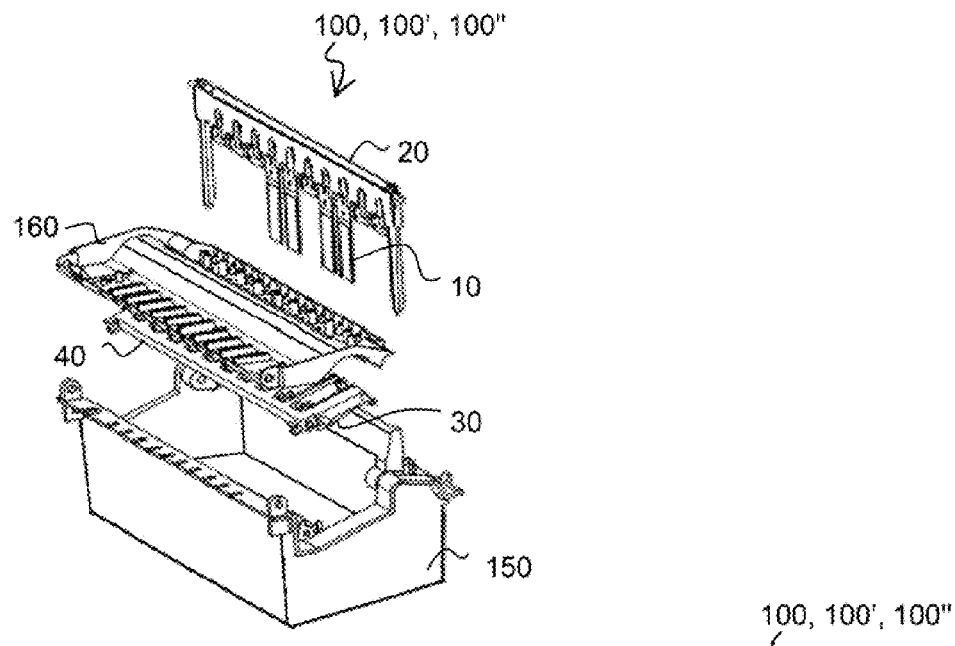
FIG. 2A is an exploded oblique view of an embodiment of an automated capillary staining module showing a processing container, a capillary lid rack, a processing container lid, and a slide rack.
Figure 2B:
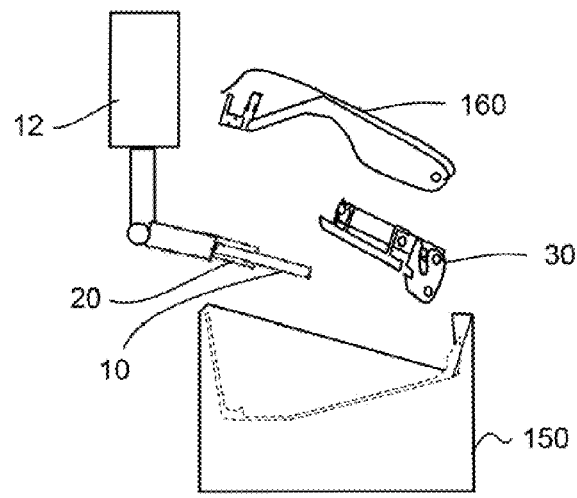
FIG. 2B is an exploded oblique view of an embodiment of an automated capillary staining module showing a processing container, a capillary lid rack, a processing container lid, and a slide rack.

FIG. 1C illustrates an orthographic view of automated staining apparatus 1. As in FIG. 1A, in the embodiments of FIG. 1C, movement of the samples on slides 10 in slide racks 20 is generally from the loading stations 17 through the various processing stations and finally to the storage units 6 which serve as unloading stations.

For IHC slides, the sample processing workflow is that slides 10 in slide rack 20 are moved by robotic arm 12 to hot plate 4 if backing is desired. Slide robot 12 moves and inserts the slide rack 20 vertically into pre-treatment module 2 for dewaxing and optionally target retrieval.

After pretreatment, slide rack 20 is moved to one of staining modules 100, 100', 100" where reagents 18a are applied according to a desired IHC protocol by fluid robot 14.

After staining, slide robot 12 moves slide rack 20 to slide storage units 6 which may be dry or may contain fluid to keep slides wet. Slide storage units 6 may be accessed by a user to unload the slide rack 20.

As schematically illustrated in FIGS. 2A, 2B, 3A, and 3B, a slide rack 20 configured to hold one or more slides 10 can be inserted into and be removed from the capillary staining module 100, 100', 100". In the embodiment shown in FIG. 2, the slide rack 20 is configured to hold a number of slides 10, e.g. ten slides 10, but it should be understood that the slide rack 20 may be configured to hold another suitable number of slides.

Further, a capillary lid rack 40 configured to hold a number of capillary lids 30 can be inserted into and be removed from the capillary staining module 100, 100', 100". In the embodiment shown in FIG. 2, the capillary lid rack 40 is configured to hold a number of capillary lids 30, e.g. ten capillary lids 30, but it should be understood that the capillary lid rack 40 may be configured to hold another suitable number of capillary lids.

The capillary staining module 100, 100', 100", comprises a processing container 150 and a processing container lid 160. As illustrated in FIG. 3A and FIG. 3B the container lid 160 is hinged at a container lid hinge 162 comprised in the processing container 150, whereby the container lid 160 can be rotated around the container lid hinge 162 in order to open and close the processing container 150. When the processing container 150 is open, the capillary lid rack 40 with the capillary lids 30 can be inserted into or removed from the processing container 150.

Further, FIG. 3A schematically illustrates a cross-sectional view of an embodiment of the capillary staining module 100, 100', 100", in which slide rack insertion and rotation is shown.

As illustrated, one or more slide racks 20 comprising one or more slides 10 are inserted into the capillary staining module 100, 100', 100" along a vertical direction as indicated by the downwards directed arrow from a position above the capillary staining module to a position at the capillary staining module.

By the dotted lines in FIG. 3A, the slide rack 20 and a slide 10 is illustrated in a position above the capillary staining module, and in a first position within the capillary staining module. In which first position, the slide is arranged along the insert direction, e.g. the vertical direction.

As further illustrated, the capillary staining module 100 comprises a slide rack holder 102 configured to hold the slide rack 20 when inserted into the capillary staining module 100, 100', 100". Further, the slide rack holder 102 is arranged at a slide rack holder hinge 104 around which hinge 104 the slide rack holder 102 is configured to rotate.

In embodiments, the slide rack holder 102 is configured to rotate between an open position, in which a slide rack 20 in an insert position, e.g. a vertical position, can be inserted into or removed from the capillary staining module 100, 100', and a closed position, in which a slide rack 20 is in an inclined position in which the slide rack 20 cannot be inserted or removed from the capillary staining module 100, 100', 100" as schematically illustrated in FIG. 3A.

The capillary staining modules 100, 100', 100" may also comprise a humidity trough 152 arranged in a lower part of the processing container 150 and configured to retain a volume of a fluid in order to provide a pre-defined or pre-determined humidity within the capillary staining module 100, 100', 100" during processing of biological samples.

As previously described, the slide robot 12, cf. FIG. 1A, is configured to move a slide rack 20 within the automated staining apparatus 1 and to insert the slide rack 20 into a capillary staining module 100, 100', 100". Further, when the slide rack 20 is arranged in the capillary staining module 100, 100', 100", electronics of the automated staining apparatus 1 are configured to automatically rotate the slide rack 20 and the one or more slides 10 around the slide rack holder hinge 104.

In embodiments, the slide rack 20 is configured to rotate from the insert position, e.g. from the vertical position, to one or more inclined positions, e.g. from an insert position A to a first inclined position B, and from the first inclined position B to a second inclined position C.

Further, FIG. 3A schematically illustrates a capillary lid rack holder 106 holding a capillary lid rack 40. The capillary lid rack holder 106 is configured to detachably hold a capillary lid rack 40. The capillary lid rack holder 106 is arranged at a capillary lid rack holder hinge 108 around which hinge 108, the capillary lid rack holder 106 can rotate. Further, the capillary lid rack holder 106 may comprise a lid rack bar 109 configured to detachably engage the lid rack 40.

In embodiments, the capillary lid rack 40 comprises an upper lid bar 42 and a middle lid bar 44 configured to hold a capillary lid 30. Further, the capillary lid rack 40 may comprise a lower bar 46 configured to detachably engage in a slot 110 of the capillary lid rack holder 106.

As schematically illustrated in FIG. 3A, the capillary lid 30 comprises a surface to be facing the upper and middle lid bars 42, 44, and fasteners 32, 34 by means of which the capillary lid 30 can be removable arranged at the capillary lid rack 40. Preferably, the fasteners 32, 34 are configured to provide a flexible attachment of the capillary lid 30 to the capillary lid rack 40 so that the distances d1 and d2 between the upper lid bar 42 and the surface of capillary lid facing the upper lid bar 42 and between the middle lid bar 44 and the surface of capillary lid facing the middle lid bar 44, respectively, can be varied.

In embodiments, the upper fastener 32 and the lower fastener 34 of the lid 30 are realised as hooks configured to detachably engage the upper lid bar 42 and the middle lid bar 44, respectively, of the capillary lid rack 40.

As schematically illustrated in FIG. 3A, in embodiments, the upper fastener 32 of the lid 30 comprises a pair hooks and the lower fastener 34 of the lid 30 comprises a single hook. However, in other embodiments, the upper fastener 32 may comprise a single hook and the lower fastener 34 may comprise a pair of hooks, or the upper and lower fasteners 32, 34 may comprise the same number of hooks. Any type of fastener such as sliding brackets, posts, and hangers may be used. Fasteners which are not rigidly and fixed attached to upper lid bar 42 and the middle lid bar 44 are beneficial in that they ride softly and evenly upon the slides.

As schematically illustrated in FIG. 3B, the embodiment illustrated functions in substantially the same way as the embodiment of FIG. 3A with the exception that in the embodiment of FIG. 3B the slide rack 20 does not rotate but is rather inserted at an angle θ with respect to the horizontal plane HP by slide robot 12. The angle θ may be in the interval of approximately 15-90 degrees to the horizontal plane HP. By orienting the slide rack at angle θ, a desired flow through timing for fluid in the capillary chamber may be achieved by adjusting the relationship between the gravitational forces and the capillary forces acting upon the fluid.

As schematically, illustrated in e.g. FIGS. 3A-6, the capillary lid 30 is arranged at the capillary lid rack 40 such that the distances d1, d2 between the surface of the capillary lid 30 facing the capillary lid rack 40 and the upper and middle capillary lid bars 42, 44 can be varied between a maximum distance, cf. FIG. 3A, and a minimum distance, cf. FIG. 6.

However, it should be understood that the distances d1, d2 do not need to be the same or changed at the same time or need to be changed at the same rate. Thus, the distance d1 may be different from the distance d2, and e.g. the distance d1 may have a maximum value while the distance d2 has a minimum value, or vice versa.

In embodiments, fluids 8a, 18a are supplied to a slide 10 when the slide is in an inclined position, e.g. when the slide 10 is in an inclined position, cf. FIGS. 4, 5, 6, 7, 9, and 11.

FIG. 4 schematically illustrates a cross-sectional view of an embodiment of the capillary staining module 100, 100', 100" in which an amount of fluid 8a, by means of the nozzle 9c, is supplied to a slide 10 in an inclined position is shown.

In embodiments, the nozzle 9c is configured with a chamfered distal end 9c', cf. e.g. FIG. 3A, configured to provide a drip free nozzle by means of which fluid 8a is not dropped on to the slide 10, but flows onto the slide 10.

As schematically illustrated by tubings 9, 9a and 9b, the fluid 8a is supplied from a fluid container (8 cf. FIG. 1A, not shown in FIG. 4) to a pre-heater 120 configured to heat the fluid passing the heater 120 to a pre-determined temperature before the fluid is supplied to the slide by means of a nozzle 9c arranged at a distal part of the tubing 9b.

It should be understood that embodiments of the capillary staining module comprises several tubings 9b and nozzles 9c, preferably one tubing 9b and one nozzle 9c for each slide that can be processed in the capillary staining module in order to provide individual supply of fluid to the each of the slides arranged in the capillary staining module.

It should also be understood that embodiments may comprise one or more tubings bypassing a possible pre-heater and a possible bubble trapper so that fluid can be supplied directly from the fluid container to the slide(s) without passing a possible pre-heater and a possible bubble trapper.

Thus, in embodiments, the automated staining apparatus 1 is configured to individually control the supply of fluid to slides arranged in the capillary staining module. For example, the fluid can be supplied to the slide(s) as a continuous fluid flow for a pre-determined time period.

The pre-heater 120 can be realised as an in-line resistive, inductive, or any type of heater including a microwave heater. By means of such a pre-heater, no heater arranged underneath the sample carrier is needed in order to heat the fluid to a desired temperature.

Alternatively a pre-heater 120 may be integrated into a bubble trapper 130 or even a plurality of bubble trappers 130 as illustrated and described below with respect to FIGS. 16A and 16B.

For some applications, e.g. such as immunohistochemical staining the pre-determined temperature of the fluid may be configured to be approximately 30 degrees Celsius in order to prevent the slide from being cooled by relatively cold rinse buffer. By keeping the slide temperature relatively constant even during rinses, the reaction rate of the immuno incubation can be made relatively consistent, thus providing more consistent staining results. However, it should be understood that for other applications, such as in-situ hybridization which may occur at 37 degrees Celsius or 50 degrees Celsius, the pre-determined temperature may be different and it may also be different for different fluids used for the application.

Embodiments of the capillary staining module 100, 100', 100" may also comprise a bubble trapper 130, cf. FIGS. 3A-12. The bubble trapper 130 can be arranged in connection with the pre-heater 120 by means of a tubing 9a or be comprised in the pre-heater 120. The bubble trapper 130 may be configured to remove bubbles from the pre-heated fluid before the pre-heated fluid is supplied to one or more slides 10 by means of a tubing 9b and the nozzle 9c.

As schematically illustrated in FIG. 3-12, the bubble trapper 130 may in some embodiments comprise an upper compartment 132 to which the heated fluid is supplied and a lower compartment 134 from which the heated fluid having possible bubbles removed exits the bubble trapper 130. The possible bubbles, such as air bubbles, will move to the upper compartment 132 from which the air bubbles can be removed by means of gas outlet (not shown). A more detailed illustration and description of an embodiment of bubble trapper 130 is described below in a section referring to FIGS. 16A and 16B.

As schematically illustrated in e.g. FIGS. 4 and 5, when an amount of a first fluid 8a has been supplied to the slide 10, the automated staining apparatus 1 is configured to control the capillary lid rack holder 106 to move the capillary lid rack 40 so that a first end 36, sometimes referred to as a lower end, of a capillary lid 30 is moved towards the corresponding slide 10 to a position in which protrusions 33 (cf. FIGS. 15A and 15B) of the first end 36 of the capillary lid 30 abut the slide 10, cf. FIG. 5.

Further, when the protrusions 33 of the first end 36 of the capillary lid 30 abut the slide 10, the automated staining apparatus 1 is configured to control the capillary lid rack holder 106 to move the capillary lid rack 40 so that a second end 38, sometimes referred to an upper end, of the capillary lid 30 is moved towards the corresponding slide 10 to a position in which protrusions 33 (cf. FIGS. 15A and 15B) of the second end 38 of the capillary lid 30 abut the slide, cf. FIG. 6.

By the movements of the first and second ends 36, 38 of the capillary lid 30, a capillary gap 31 is formed between a central recess 35 of the capillary lid 30 and a central part of the slide 10, cf. FIGS. 6, 14B, and 15. The capillary gap may function as a capillary chamber or a hybridization chamber. The capillary gap 31 may be in the range of 10-300 micrometres. In some embodiments the gap will be preferably approximately 140 micrometres. Various embodiments may be configured to provide the desired flow through rate, i.e. the rate at which an amount of fluid 8a dispensed near a higher end of slide 10 will cause a corresponding amount of fluid 8a to run off the lower end of slide 10. The dimension of the gap may be adjusted to accommodate fluids that have higher or lower viscosity, and to accommodate the slant or angle at which slide 10 is positioned with respect to the horizontal plane.

In embodiments, the lid forming the capillary gap is floating on the fluid dispensed onto the slide, whereby slide alignment issues may be avoided.

In embodiments, e.g. of an ISH capillary staining module, the automated staining apparatus 1 is configured to control the slide rack holder 102 to automatically rotate the slide rack 20 and the one or more slides 10 from the insert, e.g. vertical, position A to a first inclined position B, in which position an amount of a fluid, e.g. a reagent, is dispensed onto the slide or the biological sample by means of the probe 16 arranged in the first probe inlet 161. The automated staining apparatus 1 is further configured to control the slide rack holder 102 to automatically rotate the slide rack 20 and the one or more slides 10 from the first inclined position B to a second inclined position C. Further, when the slide(s) 10 is in the second inclined position C, the automated staining apparatus 1 is configured to control the capillary lid rack holder 106 to automatically move the capillary lid rack 40 and the capillary lid 30 so that the first end 36 of the capillary lid 30 is moved towards the corresponding slide 10 to a position in which the first end 36 abuts the slide 10 and to automatically move the second end 38 of the capillary lid 30 towards the corresponding slide 10 to a position in which the second end 38 abuts the slide 10, whereby the capillary lid 30 is arranged parallel with the slide 10 and whereby a capillary gap 31 is formed between a central recess 35 of the capillary lid 30 and a central part of the slide 10. The capillary gap 31 comprises the reagent supplied to the biological sample and thanks to the capillary gap 31 the biological sample can be processed with a small volume of reagent, e.g. a volume in the interval of 10-100 microlitres. For example, in some embodiments it may be desirable to utilize a capillary gap to process slides using 10 microlitres to 20 microlitres, or 20 microlitres to 50 microlitres in other embodiments, or 50 microlitres to 100 microliters in yet other embodiments, as desired.

FIG. 11 schematically illustrates reagent dispensing from the probe 16 onto a slide 10, when the slide 10 is arranged at a position B, e.g. at an angle larger than approximately 45 degrees to the horizontal plane. However, the slide could be arranged at another desired angle. By arranging the slide at a desired angle to the horizontal plane, the probe 16 can by means of the first probe inlet 161 be located above a desired location of the slide and thereby a desired volume of a reagent can be dispensed at the desired location of the slide 10, e.g. directly to the biological sample arranged on the slide 10 if the sample is arranged directly below the probe 16. Further, by arranging the slide at a plurality of different angles, the probe 16 can dispense a regent to a plurality of locations on the slide or the sample.

However, as schematically illustrated in FIG. 12, it should be understood that in other embodiments of e.g. an ISH capillary staining module, the reagent can be dispensed to the same location of the slide 10 as the one illustrated in FIG. 11, e.g. directly to the biological sample, also when the slide is arranged at a smaller angle to the horizontal plane, as illustrated in FIG. 12, if the processing lid 160 is provided with a second probe inlet 163 for the probe 16 at a position directly over the biological sample.

In yet other embodiments of an ISH capillary staining module, certain steps such as the dispensing of a probe onto slide 10 may take place outside the staining module, for example an ISH reagent may be dispensed onto a slide at an open horizontal station before or after insertion of the slide into the ISH capillary staining module.

In embodiments, e.g. of an IHC capillary staining module, the automated staining apparatus 1 is configured to control the slide rack holder 102 to automatically rotate the slide rack 20 and the one or more slides 10 from the vertical position A to the second inclined position C, in which position an amount of a fluid 8a, e.g. a buffer solution, is dispensed onto the slide or the biological sample by means of the nozzle 9c, cf. FIG. 4. Further, the automated staining apparatus 1 is configured to control the capillary lid rack holder 106 to automatically move the capillary lid rack 40 and the capillary lid 30 so that the first end 36 of the capillary lid 30 is moved towards the corresponding slide 10 to a position in which the first end 36 abuts the slide 10, cf. is FIG. 5, and to automatically move the second end 38 of the capillary lid 30 towards the corresponding slide 10 to a position in which the second end 38 abuts the slide 10, cf. FIG. 6, whereby the capillary lid 30 is arranged parallel with the slide 10 and whereby a capillary gap 31 is formed between a central recess 35 of the capillary lid 30 and a central part of the slide 10, the capillary gap being filled with fluid 8a supplied. The capillary gap 31 functioning as a capillary chamber.

As schematically illustrated in FIG. 7, a second fluid, e.g. a reagent 18a, is supplied to the to the slide 10 at a position above the fluid filled capillary gap 31, whereby the amount of the second fluid, due to gravity, flows into the capillary gap 31 causing fluid in the capillary gap 31 to be removed from the bottom of the capillary gap 31 and the second fluid to be drawn into the capillary gap 31 and flow downwards in the capillary gap 31 to cover the biological sample 3 arranged on the slide 10 causing the biological sample to be processed by the reagent.

In embodiments, when in the first inclined position B, the one or more slides 10 are arranged at an angle θ in the interval of approximately 20-90 degrees to the horizontal plane HP which enables an amount of reagent to be dispensed directly on a small specimen (not shown) positioned on the open face of slide 10 and approximately centered on slide 10. Thus reagent can be dispensed directly without utilizing capillary flow through for example with an ISH probe where it may be desired to dispense the probe directly rather than dispersing it in a fluid filled capillary. Further, when in the second inclined position C, the one or more slides 10 are arranged at an angle θ in the interval of approximately 10-40 degrees to the horizontal plane HP, preferably in the interval of approximately 15-30 degrees to the horizontal plane HP, and more preferably approximately 20 degrees to the horizontal plane HP, cf. FIG. 3. Additional description of embodiments suited for direct dispensing applications such as ISH are shown in FIG. 11 and FIG. 12 and described below in the detailed descriptions of FIG. 11 and FIG. 12. In certain applications, e.g. in ISH applications, the capillary gap formed is configured to function as a hybridization chamber.

As schematically illustrated in FIG. 8, the automated staining apparatus 1 may be configured to control the capillary lid rack holder 106 to automatically move the capillary lid rack 40 and the one or more capillary lids 30 back and forth in a direction parallel with the one or more slides 10, as indicated by the arrow in FIG. 8, whereby local depletion of fluid or reagent in the capillary gap 31 can be avoided and whereby fluid or reagent in the capillary gap 31 can be mixed. By avoiding depletion of fluid/reagent and/or mixing of fluid/reagent within the capillary gap 31, the processing, e.g. staining, of the biological sample exposed to the fluid/reagent within the capillary gap 31 can be improved.

Further, the automated staining apparatus 1 may be configured to control the capillary lid rack holder 106 to move the capillary lid rack 40 and the one or more capillary lids 30 along the lengthwise axis of the slide 10, and wherein in some embodiments the movement may be approximately 1 to 5 mm and have a speed of approximately 0 to 25 mm/s. The movement may be paused with the capillary lids 30 at each end position. Other embodiments may include sideways movements instead of axial lengthwise movements. Circular movements may also be used.

It should be noted that following incubation steps, a wash buffer rinse may be effected substantially as illustrated in FIG. 6. Thus with a rinse, the incubation step and corresponding reactions may be stopped and the slide may be ready to receive additional reagents e.g. a second antibody, a visualization reagent, etc. Alternatively, when a slide has been rinsed with wash buffer it may be "paused" or remain under buffer as long as desired with the capillary forces retaining the rinse buffer.

In embodiments, as schematically illustrated in FIG. 9, the staining apparatus 1 is further configured to supply an amount of fluid, e.g. a washing fluid, to the slide 10 when the capillary lid 30 is to be removed from the slide after sample processing, thereby ensuring that the lid 30, due to suction effects, does not tear off the biological sample from the slide 10 when the capillary lid 30 is removed.

As schematically illustrated in FIG. 10, one or more cleaning slides 10a arranged in a slide rack 20 may be inserted into the capillary staining module 100, 100', 100". The cleaning slide 10a comprises a number of ribs or bristles or cleansing surface 10b configured to clean a capillary lid 30 when, in use, the capillary lid 30, by means of the capillary lid rack holder 106, are moved back and forth in a direction parallel with the cleaning slide 10a, as illustrated by the arrows in FIG. 10.

In some embodiments a cleaning solution such as a DAB remover or any desired lid cleaning solution may be combined with cleaning slide 10a in order to enhance the cleaning of the lid.

In embodiments, the capillary staining module 100, 100', 100" may further be configured to prevent condensation within the module during processing. In embodiments, the processing container lid 160 may be configured to prevent condensation within the capillary staining module 100, 100', 100" and thereby configured to prevent formation of water droplets within the capillary staining module 100, 100', 100" which water droplets may cause a fluid, e.g. a reagent, dispensed to a biological sample, to be diluted during sample processing.

As schematically illustrated in FIG. 12, the processing container lid 160 may be provided with a condensation preventive layer 164 arranged on an internal surface of the processing container lid 160 facing the slides 10 and the capillary lids 30, and configured to prevent condensation within the capillary staining module 100, 100', 100". For example, the condensation preventive layer 164 may comprise aluminum or another heat conducting material or a fluid absorbing material.

In embodiments, the processing container lid 160 may comprise a heating element 168 arranged e.g. on the outside of the processing container lid 160. The heating element 168 may be configured to provide heat to the processing container lid 160 in order to prevent condensation within the capillary staining module.

FIG. 13 schematically illustrates a perspective view of an embodiment of a capillary lid rack 40 comprising ten capillary lids 30. However, it should be understood that the capillary lid rack may be configured for any number of capillary lids.

In embodiments and as schematically illustrated in FIG. 15A and FIG. 15B, the capillary lid 30 comprises, on a surface to be facing a biological sample, a central surface 35 and two protruding distal surfaces 33 (sometimes referred to as protrusions 33).

The protruding distal surfaces 33 are arranged distal of the central surface 35 and on opposite sides of the central surface 35. Further, the protruding distal surfaces 33 are configured to form spacers when in contact with a slide 10, thereby forming the previously mentioned capillary gap 31 between the central surface 35 of the capillary lid 30 and the slide 10, cf. e.g. FIG. 14B.

In the embodiment of FIG. 14C, the inlet reservoir 39' is arranged in a fork shape which may penetrate the surface of any droplet that may accumulate on the surface of, for example a slide label, thus preventing any build up and sudden release of fluid from such a droplet. One embodiment of a droplet catching form for a inlet reservoir is illustrated in FIG. 15B.

The capillary lid 30 may comprise glass and the protruding distal surfaces/spacers 33 may comprise one or more layers of paint or another suitable material having a pre-defined thickness in order to provide an accurate distance between the central surface 35 of the capillary lid 30 and the slide 10.

However, it should be understood that the capillary lid 30 may be moulded in a plastic material, such as polycarbonate, or another suitable material.

As schematically illustrated in FIGS. 15A and 15B, the capillary lid 30 is provided with a chamfered surface 39 in an upper central part. The chamfered surface 39 is configured to function as an inlet reservoir 39 into the capillary gap 31, when in use, the capillary lid 30 is arranged at the slide 10. The inlet reservoir 39 is configured to retain a predefined fluid/reagent volume, such as a volume up to approximately 300 microlitres.

In embodiments and as schematically illustrated in FIGS. 15A and 15B, the capillary lid 30 is provided with a drip tip 37 in a lower central part of the capillary lid 30. The drip tip 37 is configured to provide a controlled removal of fluid from the lower part of the capillary gap 31. By means of the drip tip 37 an even fluid front of fluid/reagent supplied to the upper part of the capillary gap is accomplished, cf. FIG. 14B as compared to the uneven fluid front within a capillary gap created between a slide 10 and a lid 30 without drip tip, as illustrated in FIG. 14A.

FIG. 16A is an exploded view of an embodiment of a combination fluid heater/dual bubble trapper 130'. A heater 120 includes a heating element 121 and a temperature sensor 122 to control the temperature. The heater 120 may be made of aluminum or other materials with desired heat conducting properties. Non-reactive plates 123, 125 may be arranged on both sides of heater 120 so that fluid is heated by heater 120 but does not come in direct contact with heater 120. Suitable materials for non-reactive plates may include stainless steel or other thermally conductive materials such as thermally conductive polymers that are non-reactive with the fluids that may be heated by the heater 120.

In an embodiment, a first bubble trapper 139 and a second bubble trapper 139' may be included in combination fluid heater/bubble trapper 130'. This enables bubble trapper 139 to be used for heating and removing bubbles from a first fluid, for example distilled water, and second bubble trapper 139' to be used for heating and removing bubbles from a second fluid, for example a wash buffer.

As schematically illustrated in FIG. 16B, the bubble trappers 139 and 139' shown in FIG. 16A function as follows. A fluid 140 enters bubble trapper 139 through inlet 134 and flows past baffle 133 to exit through outlets 135 and 137. Any bubbles 131 that may have formed within the fluid will rise to the upper half 136 of the bubble trap and travel up to bubble outlet 132. Outlet 132 may be closed by a valve so that the pressure of the enclosed air prevents fluid from flowing out through outlet 132. Then at a desired time, outlet 132 may be opened to allow accumulated bubbles 131 to vent.

What is claimed is:

1. An automated staining apparatus for processing at least one biological sample arranged on a slide, the apparatus comprising:
    at least one capillary staining module comprising:
        a slide rack holder configured to detachably hold a slide rack configured to hold one or more slides, and
        a capillary lid rack holder configured to detachably hold a capillary lid rack configured to hold one or more capillary lids, wherein the slide rack can be removed from the apparatus independently of removing the capillary lid rack from the apparatus, and
        a first fluid container comprising a first fluid,
    wherein the automated staining apparatus is configured to automatically:
        control the slide rack holder to rotate the one or more slides from an insert position to one or more inclined position, and control the capillary lid rack holder to move the one or more capillary lids towards the one or more slides to automatically form a capillary gap between each slide and each capillary lid, said capillary gap functioning as a capillary chamber; and to automatically
        supply an amount of the first fluid from the fluid container to the slide when in said inclined position.

2. The apparatus of claim 1, wherein the automated staining apparatus is further configured to automatically:
    control the capillary lid rack holder to move a first end of a capillary lid towards a corresponding slide so that the first end of the capillary lid abuts the slide, and to move a second end of the capillary lid towards the corresponding slide so that the second end of the capillary lid abuts the slide, whereby a capillary gap is formed between a central recess of the capillary lid and a central part of the slide, the capillary gap being configured to comprise the supplied first fluid.

3. The apparatus of claim 1 further comprising a probe configured to aspirate an amount of a reagent contained in a reagent container, wherein the probe is further configured to directly supply, via a probe inlet of the capillary staining module, the amount of a reagent as the first fluid to the biological sample arranged on the slide, whereby the capillary gap formed can function as a hybridization chamber.

4. The apparatus of claim 1, wherein the automated staining apparatus is further configured to:
    supply, via a probe inlet or a nozzle, an amount of a second fluid from a second fluid container to the slide at a position above the fluid filled capillary gap, whereby the amount of the second fluid, due to gravity, flows into the capillary gap causing an amount of the first fluid in the capillary gap to be removed from the bottom of the capillary gap and the second fluid to be drawn into the capillary gap and flow downwards in the capillary gap to cover the biological sample arranged on the slide.

5. The apparatus of claim 4, wherein the first fluid is a washing fluid and the second fluid is a reagent.

6. The apparatus of claim 4, wherein the one or more sample slides when in the inclined position is arranged at an angle in the interval of approximately 10-40 degrees to the horizontal plane.

7. The apparatus of claim 1, further comprising one or more tubings connected to one or more fluid containers, the tubings comprise in a distal part one or more nozzles for dispensing a fluid to the one or more slides, the nozzle is configured with a chamfered distal end opening to provide a drip free nozzle by means of which fluid is not dropped on to the slide, but flows onto the slide.

8. The apparatus of claim 7, further comprising one or more pumps and one or more valves connected to the tubings and by means of which the automated staining apparatus is configured to control the supply of fluid from the one or more fluid containers to the one or more slides.

9. The apparatus of claim 1, further comprising a fluid robot configured to operate a probe:
    to aspirate a portion of a reagent contained in a reagent container within the automated staining apparatus;
    to transfer the aspirated portion of the reagent to a position above a slide or a biological sample, wherein the slide or the biological sample is contained within the at least one capillary staining module;
    to dispense an amount of the aspirated portion of the reagent to the slide or the biological sample.

10. The apparatus of claim 1, wherein the automated staining apparatus is configured to control the capillary lid rack holder to automatically move one or more capillary lids back and forth in a direction parallel with the one or more sample slides, whereby local depletion of the fluid in the capillary gap is avoided and/or the fluid in the capillary gap is mixed.

11. The apparatus of claim 10, wherein the automated staining apparatus is configured to control the capillary lid rack holder to move the one or more capillary lids along the lengthwise axis of the slide.

12. The apparatus of claim 1, wherein the automated staining apparatus is configured to:
    supply an amount of a fluid to the slide when the capillary lid is to be removed after sample processing, thereby ensuring that the capillary lid, due to suction effects, does not tear off the biological sample from the slide when the capillary lid is removed.

13. The apparatus of claim 1, further comprising a pre-heater configured to heat the fluid to a pre-determined temperature before the fluid is dispensed to the slide.

14. The apparatus of claim 13, further comprising a bubble trapper arranged in connection with or comprised in the pre-heater and configured to remove bubbles from the pre-heated fluid before the pre-heated fluid is supplied to the slide.

15. The apparatus of claim 1, wherein the capillary lid on a surface to be facing a biological sample comprises a central surface and two protruding distal surfaces, the protruding distal surfaces being arranged distal of the central surface and on opposite sides of the central surface, the protruding distal surfaces are configured to form spacers when in contact with a sample slide, the protruding distal surfaces having a pre-defined thickness in order to provide an exact distance between the central surface of the capillary lid and the slide when the protruding distal surfaces of the lid abut the slide, thereby forming the well-defined capillary gap between the central surfaces of the capillary lid and the slide.

16. The apparatus of claim 15, wherein the capillary lid comprises glass and wherein the protruding distal surfaces comprise one or more layers of paint having a pre-defined thickness.

17. The apparatus of claim 15, wherein the capillary lid is moulded in a polycarbonate.

18. The apparatus of claim 15, wherein the capillary lid in an upper central part is provided with a chamfered surface functioning as an inlet reservoir into the capillary gap, when in use, the protruding distal surfaces of the capillary lid abut the slide.

19. The apparatus of claim 15, wherein the capillary lid in a lower central part is provided with a drip tip, the drip tip being configured to provide a controlled removal of fluid from the lower part of the capillary gap, whereby an even fluid front supplied to the upper part of the capillary gap can be accomplished.

20. The apparatus of claim 1, wherein the capillary staining module comprises a humidity trough arranged in a lower part of a processing container of the capillary staining module, the humidity trough being configured to retain a liquid volume and thereby preventing evaporation of fluid within the capillary staining module.

21. The apparatus of claim 1, wherein the capillary staining module further comprises a processing container lid configured to prevent condensation within the capillary staining module and thereby configured to prevent formation of water droplets within the capillary staining module, which water droplets may cause a fluid dispensed to a biological sample to be diluted during sample processing.

22. The apparatus of claim 21, wherein the processing container lid is provided with a condensation preventive layer arranged on an internal surface of the processing container lid, the condensation preventive layer is configured to prevent condensation within the capillary staining module.

23. The apparatus of claim 22, wherein the condensation preventive layer comprises aluminum or another heat conducting material or a fluid absorbing material.

24. The apparatus of claim 21, wherein the processing container lid is provided with a heating element arranged on the outside of the processing container lid and configured to provide heat to the processing container lid in order to prevent condensation within the capillary staining module.

25. The apparatus of claim 1, wherein a slide rack comprising one or more cleaning slides can be detachably arranged in the slide rack holder, the cleaning slides being provided with a cleansing surface configured to clean one or more capillary lids when, in use, the one or more capillary lids are moved back and forth in a direction parallel with the cleaning slides.

26. An automated method for processing at least one biological sample arranged on a slide, the method comprises:
    providing at least one capillary staining module comprising:
        a slide rack holder configured to detachably hold a slide rack configured to hold one or more slides, and
        a capillary lid rack holder configured to detachably hold a capillary lid rack configured to hold one or more capillary lids, wherein the slide rack can be removed from the apparatus independently of removing the capillary lid rack from the apparatus,
        providing a first fluid container comprising a first fluid,
        automatically controlling the slide rack holder to rotate the one or more slides from an insert position to one or more inclined positions; and
        automatically controlling the capillary lid rack holder to move the one or more capillary lids towards the one or more slides to automatically form a capillary gap between each slide and each capillary lid, said capillary gap functioning as a capillary chamber; and
        automatically supplying an amount of the first fluid from the fluid container to the slide when in said inclined position.

27. The method of claim 26, further comprising:
controlling the capillary lid rack holder to move a first end of a capillary lid towards a corresponding slide so that the first end of the capillary lid abuts the slide, and to move a second end of the capillary lid towards the corresponding slide so that the second end of the capillary lid abuts the slide, whereby a capillary gap is formed between a central recess of the capillary lid and a central part of the slide, the capillary gap comprising the supplied first fluid.

28. The method of claim 26, further comprising:
using a probe to aspirate an amount of a regent from a reagent contained within the apparatus; and
directly supplying, via a probe inlet of the capillary staining module, the amount of the reagent as the first fluid to the biological sample arranged on the slide, whereby the capillary gap formed can function as a hybridization chamber.

29. The method of claim 27, further comprising:
using a probe positioned within the apparatus to aspirate an amount of a reagent from a reagent contained within the apparatus; and
directly supplying, via a probe inlet of the capillary staining module, the amount of the reagent as the first fluid to the biological sample arranged on the slide, whereby the capillary gap formed can function as a hybridization chamber.

30. The method of claim 27, further comprising:
supplying, via a probe inlet or a nozzle, an amount of a second fluid from a second fluid container to the slide at a position above the fluid filled capillary gap, whereby the amount of the second fluid, due to gravity, flows into the capillary gap causing an amount of the first fluid in the capillary gap to be removed from the bottom of the capillary gap and the second fluid to be drawn into the capillary gap and flow downwards in the capillary gap to cover the biological sample arranged on the slide.

31. The method of claim 30, wherein the one or more sample slides when in the inclined position is arranged at an angle in the interval of approximately 10-40 degrees to the horizontal plane.

32. The method of claim 26, further comprising:
providing one or more tubings connected to one or more fluid containers, the tubings comprise in a distal part one or more nozzles for dispensing a fluid to the one or more slides, the nozzle is configured with a chamfered distal end opening to provide a rip free nozzle by means of which fluid is not dropped on to the slide, but flows onto the slide.

33. The method of claim 32, further comprising:
by means of one or more pumps and one or more valves connected to the tubings, controlling the supply of fluid from the one or more fluid containers to the one or more slides.

34. The method of claim 26, further comprising:
by means of a fluid robot configured to operate a probe:
    aspirating a portion of a reagent contained in a reagent container within the automated staining apparatus;
    transferring the aspirated portion of the reagent to a position above a slide or a biological sample, wherein the slide or the biological is contained within the at least one capillary staining module; and dispensing an amount of the aspirated portion of the reagent to the slide or the biological sample.

35. The method of claim 26, further comprising:

controlling the capillary lid rack holder to automatically move one or more capillary lids back and forth in a direction parallel with the one or more sample slides, whereby local depletion of the fluid in the capillary gap is avoided and/or the fluid in the capillary gap is mixed.

36. The method of claim 35, further comprising:

controlling the capillary lid rack holder to move the one or more capillary lids along the lengthwise axis of the slide.

37. The method of claim 26, further comprising:

supplying an amount of a fluid to the slide when the capillary lid is to be removed after sample processing, thereby ensuring that the capillary lid, due to suction effects, does not tear off the biological sample from the slide when the capillary lid is removed.

38. The method of claim 26, further comprising:

by means of a pre-heater, heating the fluid to a pre-determined temperature efore the fluid is dispensed to the slide.

39. The method of claim 38, further comprising:

by means of a bubble trapper arranged in connection with or comprised in the pre-heater, removing bubbles from the pre-heated fluid before the pre-heated fluid is supplied to the slide.

40. The method of claim 26, further comprising:

by means of a drip tip arranged in a lower central part of the capillary lid, controlling removal of fluid from the lower part of the capillary gap, whereby an even fluid front supplied to the upper part of the capillary gap can be accomplished.

41. The method of claim 26, further comprising:

by means of a humidity trough configured to retain a liquid volume and arranged in a lower part of a processing container of the capillary staining module, preventing evaporation of fluid within the capillary staining module.

42. The method of claim 26, further comprising:

by means of a processing container lid comprised in the capillary staining module, preventing condensation within the capillary staining module and thereby preventing formation of water droplets within the capillary staining module, which water droplets may cause a fluid dispensed to a biological sample to be diluted during sample processing.

43. The method of claim 26, further comprising:

by means of one or more cleaning slides comprising a cleansing surface, cleaning one or more capillary lids when, in use, the one or more capillary lids are moved back and forth in a direction parallel with the cleaning slides.

* * * * *

UNITED STATES PATENT AND TRADEMARK OFFICE
CERTIFICATE OF CORRECTION

PATENT NO. : 8,877,485 B2
APPLICATION NO. : 12/962825
DATED : November 4, 2014
INVENTOR(S) : Søren Damgaard Larsen et al.

It is certified that error appears in the above-identified patent and that said Letters Patent is hereby corrected as shown below:

In the Claims

Claim 34, Col. 21, Line 1, "biological" should read as --biological sample--.

Claim 38, Col. 21, Line 22, "efore" should read as --before--.

Signed and Sealed this
Seventeenth Day of March, 2015

Michelle K. Lee
*Director of the United States Patent and Trademark Office*